US006960566B1

(12) United States Patent
Blaszczyk-Thurin

(10) Patent No.: US 6,960,566 B1
(45) Date of Patent: Nov. 1, 2005

(54) COMPOSITIONS AND METHODS FOR TREATMENT OF CANCER

(75) Inventor: Magdalena Blaszczyk-Thurin, Philadelphia, PA (US)

(73) Assignees: The Wister Institute of Anatomy and Biology, Philadelphia, PA (US); The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/831,047

(22) PCT Filed: Nov. 5, 1999

(86) PCT No.: PCT/US99/26277

§ 371 (c)(1),
(2), (4) Date: May 3, 2001

(87) PCT Pub. No.: WO00/27420

PCT Pub. Date: May 18, 2000

Related U.S. Application Data

(60) Provisional application No. 60/107,478, filed on Nov. 6, 1998.

(51) Int. Cl.[7] ............................ A61K 38/00; C07K 5/00
(52) U.S. Cl. ........................................ 514/14; 530/300
(58) Field of Search .................... 514/2, 14, 1; 530/300

(56) References Cited

U.S. PATENT DOCUMENTS

| 5,464,935 | A | * | 11/1995 | Heavner et al. ............ 530/329 |
| 5,602,230 | A | | 2/1997 | Heavner et al. |
| 5,614,615 | A | * | 3/1997 | Wong ........................ 536/17.9 |
| 5,618,785 | A | | 4/1997 | Heavner et al. |
| 5,639,734 | A | * | 6/1997 | Esko et al. .................... 514/25 |
| 5,643,873 | A | | 7/1997 | Barrett et al. |
| 5,861,505 | A | | 1/1999 | Kern |
| 2003/0017497 | A1 | | 1/2003 | Keiber-Emmons et al. |

OTHER PUBLICATIONS

MJ Polley, ML Phillips, E Wayner, E Nudelman, AK Singhal, S Hakomori, and JC Paulson CD62 and Endothelial Cell–Leukocyte Adhesion Molecule 1 (ELAM–1) Recognize the Same Carbohydrate Ligand, Sialyl–Lewis x PNAS 1991 88: 6224–6228.*
R. Radinsky et al, "Regulation of Tumor Cell Growth at Organ Specific Metastases", in vivo, 6:325–332 (1992).
G. Nicolson, "Metastatic Tumor Cell Interactions with Endothelium, Basement Membrane and Tissue", Current Opinion in Cell Biology, 1:1009–1019 (1989).
M. Bevilacqua et al, "Endothelial Leukocyte Adhesion Molecule 1: An Inducible Receptor for Neutrophils Related to Complement Regulatory Proteins and Lectins", Science, 243:1160–1165 (Mar., 1989).
P. Brodt, "Adhesion Receptors and Proteolytic Mechanisms in Cancer Invasion and Metastasis", in Cell Adhesion and Invasion in Cancer Metastasis, ed. by P. Brodt, Chapter 11, pp. 167–242 (1996).

E. Butcher et al, "Lymphocyte Homing and Homeostasis", Science, 272:60–66 (Apr., 1996).
L. Lasky, "Selectin–Carbohydrate Interactions and the Initiation of the Inflammatory Response", Annu. Rev. Biochem., 64:113–139 (1995).
A. Varki, "Selectin Ligands", Proc. Natl. Acad. Sci. USA, 91:7390–7397 (Aug., 1994).
M. Bevilacqua et al, "Selectins", J. Clin. Invest., 91:379–387 (Feb., 1993).
G. Mannori et al, "Differential Colon Cancer Cell Adhesion to E–, P–, and L–selectin: Role of Mucin–type Glycoproteins", Cancer Research, 55:4425–4431 (Oct., 1995).
S. Karpatkin et al, "Role of Platelets in Tumor Cell Metastases", Annals of Internal Medicine, 95:636–641 (Nov., 1981).
D. Welch et al, "Tumor–elicited Polymorphonuclear Cells, in Contrast to 'Normal' Circulating Polymorphonuclear Cells, Stimulate Invasive and Metastatic Potentials of Rat Mammary Adenocarcinoma Cells", Proc. Natl. Acad. Sci. USA, 86:5859–5863 (Aug., 1989).
A. Seth et al, "T–Cell–Receptor–Independent Activation of Cytolytic Activity of Cytotoxic T Lymphocytes Mediated Through CD44 and gp90$^{MEL-14}$", Proc. Natl. Acad. Sci. USA, 88:7877–7881 (Sep., 1991).
F. Kolbinger et al, "The Carbohydrate–Recognition Domain of E–Selectin is Sufficient for Ligand Binding Under Both Static and Flow Conditions", Biochemistry. 35:6385–6392 (1996).
B. Revelle et al, "Single Amino Acid Residues in the E– and P–selectin Epidermal Growth Factor Domains Can Determine Carbohydrate Binding Specificity", J. Biol. Chem., 271(27):16160–16170 (Jul., 1996).
S. Li et al, "Consensus Repeat Domains of E–selectin Enhance Ligand Binding", J. Biol. Chem, 269(6):4431–4437 (Feb., 1994).
D. Erbe et al, "P– and E–Selectin Use Common Sites for Carbohydrate Ligand Recognition and Cell Adhesion", J. Cell Biol., 120(5):1227–1235 (Mar., 1993).
B. Graves et al, "Insight into E–selectin/ligand Interaction from the Crystal Structure and Mutagenesis of the lec/EGF Domains", Nature, 367:532–538 (Feb., 1994).
R. Giavazzi et al, "Rolling and Adhesion of Human Tumor Cells on Vascular Endothelium under Physiological Flow Conditions", J. Clin. Invest., 92:3038–3044 (Dec., 1993).

(Continued)

*Primary Examiner*—Jon Weber
(74) *Attorney, Agent, or Firm*—Howson and Howson

(57) ABSTRACT

Compositions containing one or more peptido-mimetics or modified peptido-mimetics of a carbohydrate ligand of an adhesion molecule in a physiologically acceptable carrier are useful for methods of reducing metastasis in a mammal and for inhibiting inflammatory response in a mammal. Particularly useful are embodiments in which the ligand is a Lewis antigen and/or the adhesion molecule is a selectin, e.g, E-selectin. Methods are disclosed for identifying peptido-mimetics of carbohydrate ligands, which may be involved in binding of tumor cells to other cells, such as endothelial cells.

4 Claims, 5 Drawing Sheets

OTHER PUBLICATIONS

E. Dejana et al, "Endothelial Leukocyte Adhesion Molecule–1–Dependent Adhesion of Colon Carcinoma Cells to Vascular Endothelium is Inhibited by an Antibody to Lewis Fucosylated Type I Carbohydrate Chain", Laboratory Investigation, 66(3):324–330 (1992).

A. Takada et al, "Contribution of Carbohydrate Antigens Sialyl Lewis A and Sialyl Lewis X to Adhesion of Human Cancer Cells to Vascular Endothelium", Cancer Research, 53:354–361 (Jan., 1993).

R. Sawada et al, "Differential E–selectin–dependent Adhesion Efficiency in Sublines of a Human Colon Cancer Exhibiting Distinct Metastatic Potentials", J. Biol. Chem., 269(2):1425–1431 (Jan., 1994).

P. Brodt et al, "Liver Endothelial E–Selectin Mediates Carcinoma Cell Adhesion and Promotes Liver Metastasis", Int. J. Cancer, 71:612–619 (1997).

G. Mannori et al, "Inhibition of Colon Carcinoma Cell Lung Colony Formation by a Soluble Form of E–Selectin", American Journal of Pathology 151(1):233–243 (Jul., 1997).

L. Biancone et al, "Redirection of Tumor Metastasis by Expression of E–Selectin in Vivo", J. Exp. Med., 183:581–587 (Feb., 1996).

K. Iwai et al, "Importance of E–Selectin (ELAM–1) and Sialyl Lewis$^a$ in the Adhesion of Pancreatic Carcinoma Cells to Activated Endothelium", Int. J. Cancer, 54:972–977 (1993).

A. Tözeren et al, "E–Selectin–Mediated Dynamic Interactions of Breast– and Colon–Cancer Cells with Endothelial-Cell Monolayers", Int. J. Cancer, 60:426–431 (1995).

M. Miyake et al, "Correlation of Expression of H/Le$^y$/Le$^b$ Antigens with Survival in Patients with Carcinoma of the Lung", N. Engl. J. Med., 327:14–18 (Jul., 1992).

J. Garrigues et al, "Anti–Tumor Antibody BR96 Blocks Cell Migration and Binds to a Lysosomal Membrane Glycoprotein on Cell Surface Microspikes and Ruffled Membranes", J. Cell Biol., 125(1):129–142 (Apr., 1994).

G. Kansas, "Selectins and Their Ligands: Current Concepts and Controversies", Blood, 88(9):3259–3287 (Nov., 1996).

D. Ingber et al, "Mechanochemical Switching Between Growth and Differentiation During Fibroblast Growth Factor–Stimulated Angiogenesis in Vitro: Role of Extracellular Matrix", J. Cell. Biol., 109:317–330 (Jul., 1989).

M. Nguyen et al, "1–Deoxymannojirimycin Inhibits Capillary Tube Formation in Vitro", J. Biol. Chem., 267(36):26157–26165 (Dec., 1992).

J. Folkman, "Clinical Applications of Research on Angiogenesis", N. Engl. J. Med., 333(26):1757–1763 (Dec., 1995).

M. Agadjanyan et al, "Peptide Mimicry of Carbohydrate Epitopes on Human Immunodeficiency Virus", Nature Biotechnology 15:547–551 (Jun., 1997).

T. Tsukida et al, "Studies on Selectin Blockers. 7. Structure–Activity Relationships of Sialyl Lewis X Mimetics Based on Modified Ser–Glu Dipeptides", J. Med. Chem., 41:4279–4287 (1998).

D. Ishikawa et al, "GD1α–replica Peptides Functionally Mimic CG1α, an Adhesion Molecule of Metastatic Tumor Cells, and Suppress the Tumor Metastasis", FEBS Letters, 441:20–24 (1998).

Bechtel et al., "Conformational analysis of the tumor–associated carbohydrate antigen 19–9 and its Lea blood group antigen component as related to the specificity of monoclonal antibody CO19–9", J. Biol. Chem. Feb. 5, 1990 265(4):2028–2037.

Blaszczyk et al., "Characterization of gastrointestinal tumor–associated carcinoembryonic antigen–related antigens defined by monoclonal antibodies", Cancer Res. Jan. 1984 44(1):245–253.

Blaszczyk et al., "Characterization of Lewis antigens in normal colon and gastrointestinal adenocarcinomas", Proc. Natl. Acad. Sci. USA Jun. 1985 82(11):3552–3556.

Blaszczyk et al., "Lewis blood group antigens defined by monoclonal anti–colon carcinoma antibodies", Arch. Biochem. Biophys. Aug. 15, 1984 233(1):161–168.

Blaszczyk–Thurin et al., "Biosynthetic pathways for the Leb and Y glycolipids in the gastric carcinoma cell line KATO III as analyzed by a novel assay", Biochem. Biophys. Res. Commun. Feb. 29, 1988 151(1):100–108.

Blaszczyk–Thurin et al., "Y and blood group B type 2 glycolipid antigens accumulate in a human gastric carcinoma cell line as detected by monoclonal antibody. Isolation and characterization by mass spectrometry and NMR spectroscopy", J. Biol. Chem. Jan. 5, 1987 262(1):372–379.

Fukushi et al., "Location and distribution of difucoganglioside (V13NeuAcV3III3Func2nLc6) in normal and tumor tissues defined by its monoclonal antibody FH6", Cancer Res. Aug. 1985 45(8):3711–3717.

Geng et al., Lectin domain peptides from selectins interact with both cell surface ligands and Ca2+ ions',J. Biol. Chem. Oct. 5, 1992 267(28):19846–19853.

Hansson et al., "Mouse monoclonal antibodies against human cancer cell lines with specificities for blood group and related antigens. Characterization by antibody binding to glycosphingolipids in a chromatogram binding assay", J. Biol. Chem. Apr. 10, 1983 258(7):4091–4097.

Hoess et al., "Identification of a peptide which binds to the carbohydrate–specific monoclonal antibody B3", Gene Jun. 15, 1993 128(1):43–49.

Kaur et al., "Topological analysis of the functional mimicry between a peptide and a carbohydrate moiety", J. Biol. Chem. Feb. 28, 1997 272(9):5539–5543.

Magnani et al., "A monosialoganglioside is a monoclonal antibody–defined antigen of colon carcinoma", Science Apr. 3, 1981 212 (4490):55–56.

Martens et al., "Peptides which bind to E–selectin and block neutrophil adhesion", J. Biol. Chem. Sep. 8, 1995 270(36):21129–21136.

Murali et al., "Molecular recognition of a peptide mimic of the Lewis Y antigen by an anti–Lewis Y antibody", J. Mol. Recog. Nov.–Dec. 1997 10(6):269–276.

Pastan et al., "Characterization of monoclonal antibodies B1 and B3 that react with mucinous adenocarcinomas", Cancer Res. Jul. 15, 1991 51(14):3781–3787.

Rao et al., "Sialyl Lewis X mimics derived from a pharmacophore search are selectin inhibitors with anti–inflammatory activity", J. Biol. Chem. Aug. 5, 1994 269(31):19663–19666.

Rodeck et al., "A mucin containing the X, Y, and H type 2 carbohydrate determinants is shed by carcinoma cells", Hybridoma Aug. 1987 6(4):389–401.

Staite et al., "Inhibition of delayed–type contact hypersensitivity in mice deficient in both E–selectin and P–selectin", *Blood* Oct. 15, 1996 88(8):2973–2979.

Steplewski et al., "Isolation and characterization of anti-monosialoganglioside monoclonal antibody 19–9 class–switch variants", *Proc. Natl. Acad. Sci. USA* Dec. 1985 82(24):8653–8657.

Blaszczyk–Thurin et al., "Molecular recognition of the Lewis Y antigen by monoclonal antibodies", *Protein Eng.* May 1996 9(5):447–459.

* cited by examiner

SEQUENCE LISTING

<160> NUMBER OF SEQ ID NOS: 121

<210> SEQ ID NO 1
<211> LENGTH: 12
<212> TYPE: PRT
<213> ORGANISM: peptido-mimetic of a Lewis antigen

<400> SEQUENCE: 1

Asp Leu Trp Asp Trp Val Val Gly Lys Pro Ala Gly
1               5                   10

<210> SEQ ID NO 2
<211> LENGTH: 12
<212> TYPE: PRT
<213> ORGANISM: peptido-mimetic of a Lewis antigen

<400> SEQUENCE: 2

Asp Ala Trp Asp Trp Val Val Gly Lys Pro Ala Gly
1               5                   10

<210> SEQ ID NO 3
<211> LENGTH: 12
<212> TYPE: PRT
<213> ORGANISM: peptido-mimetic of a Lewis antigen

<400> SEQUENCE: 3

Asp Asp Trp Asp Trp Val Val Gly Lys Pro Ala Gly
1               5                   10

<210> SEQ ID NO 4
<211> LENGTH: 12
<212> TYPE: PRT
<213> ORGANISM: peptido-mimetic of a Lewis antigen

<400> SEQUENCE: 4

Asp Tyr Trp Asp Trp Val Val Gly Lys Pro Ala Gly
1               5                   10

<210> SEQ ID NO 5
<211> LENGTH: 12
<212> TYPE: PRT
<213> ORGANISM: peptido-mimetic of a Lewis antigen

<400> SEQUENCE: 5

Asp Glu Trp Asp Trp Val Val Gly Lys Pro Ala Gly
1               5                   10

<210> SEQ ID NO 6
<211> LENGTH: 12
<212> TYPE: PRT
<213> ORGANISM: peptido-mimetic of a Lewis antigen

<400> SEQUENCE: 6

Asp Lys Trp Asp Trp Val Val Gly Lys Pro Ala Gly
1               5                   10

<210> SEQ ID NO 7
<211> LENGTH: 12
<212> TYPE: PRT
<213> ORGANISM: peptido-mimetic of a Lewis antigen

<400> SEQUENCE: 7

Asp Arg Trp Asp Trp Val Val Gly Lys Pro Ala Gly

```
                      -continued
1               5                   10

<210> SEQ ID NO 8
<211> LENGTH: 12
<212> TYPE: PRT
<213> ORGANISM: peptido-mimetic of a Lewis antigen

<400> SEQUENCE: 8

Asp Ser Trp Asp Trp Val Val Gly Lys Pro Ala Gly
1               5                   10

<210> SEQ ID NO 9
<211> LENGTH: 12
<212> TYPE: PRT
<213> ORGANISM: peptido-mimetic of a Lewis antigen

<400> SEQUENCE: 9

Asp Leu His Asp Trp Val Val Gly Lys Pro Ala Gly
1               5                   10

<210> SEQ ID NO 10
<211> LENGTH: 12
<212> TYPE: PRT
<213> ORGANISM: peptido-mimetic of a Lewis antigen

<400> SEQUENCE: 10

Asp Leu Tyr Asp Trp Val Val Gly Lys Pro Ala Gly
1               5                   10

<210> SEQ ID NO 11
<211> LENGTH: 12
<212> TYPE: PRT
<213> ORGANISM: peptido-mimetic of a Lewis antigen

<400> SEQUENCE: 11

Asp Leu Phe Asp Trp Val Val Gly Lys Pro Ala Gly
1               5                   10

<210> SEQ ID NO 12
<211> LENGTH: 12
<212> TYPE: PRT
<213> ORGANISM: peptido-mimetic of a Lewis antigen

<400> SEQUENCE: 12

Asp Leu Met Asp Trp Val Val Gly Lys Pro Ala Gly
1               5                   10

<210> SEQ ID NO 13
<211> LENGTH: 12
<212> TYPE: PRT
<213> ORGANISM: peptido-mimetic of a Lewis antigen

<400> SEQUENCE: 13

Asp Leu Ala Asp Trp Val Val Gly Lys Pro Ala Gly
1               5                   10

<210> SEQ ID NO 14
<211> LENGTH: 12
<212> TYPE: PRT
<213> ORGANISM: peptido-mimetic of a Lewis antigen

<400> SEQUENCE: 14

Asp Leu Glu Asp Trp Val Val Gly Lys Pro Ala Gly
1               5                   10
```

```
<210> SEQ ID NO 15
<211> LENGTH: 12
<212> TYPE: PRT
<213> ORGANISM: peptido-mimetic of a Lewis antigen

<400> SEQUENCE: 15

Asp Leu Asp Asp Trp Val Val Gly Lys Pro Ala Gly
1               5                   10

<210> SEQ ID NO 16
<211> LENGTH: 12
<212> TYPE: PRT
<213> ORGANISM: peptido-mimetic of a Lewis antigen

<400> SEQUENCE: 16

Asp Leu Lys Asp Trp Val Val Gly Lys Pro Ala Gly
1               5                   10

<210> SEQ ID NO 17
<211> LENGTH: 12
<212> TYPE: PRT
<213> ORGANISM: peptido-mimetic of a Lewis antigen

<400> SEQUENCE: 17

Asp Leu Arg Asp Trp Val Val Gly Lys Pro Ala Gly
1               5                   10

<210> SEQ ID NO 18
<211> LENGTH: 12
<212> TYPE: PRT
<213> ORGANISM: peptido-mimetic of a Lewis antigen

<400> SEQUENCE: 18

Asp Leu Ser Asp Trp Val Val Gly Lys Pro Ala Gly
1               5                   10

<210> SEQ ID NO 19
<211> LENGTH: 12
<212> TYPE: PRT
<213> ORGANISM: peptido-mimetic of a Lewis antigen

<400> SEQUENCE: 19

Asp Leu Trp Glu Trp Val Val Gly Lys Pro Ala Gly
1               5                   10

<210> SEQ ID NO 20
<211> LENGTH: 12
<212> TYPE: PRT
<213> ORGANISM: peptido-mimetic of a Lewis antigen

<400> SEQUENCE: 20

Asp Leu Trp Ser Trp Val Val Gly Lys Pro Ala Gly
1               5                   10

<210> SEQ ID NO 21
<211> LENGTH: 12
<212> TYPE: PRT
<213> ORGANISM: peptido-mimetic of a Lewis antigen

<400> SEQUENCE: 21

Asp Leu Trp Pro Trp Val Val Gly Lys Pro Ala Gly
1               5                   10

<210> SEQ ID NO 22
```

```
<211> LENGTH: 12
<212> TYPE: PRT
<213> ORGANISM: peptido-mimetic of a Lewis antigen

<400> SEQUENCE: 22

Asp Leu Trp Val Trp Val Val Gly Lys Pro Ala Gly
1               5                   10

<210> SEQ ID NO 23
<211> LENGTH: 12
<212> TYPE: PRT
<213> ORGANISM: peptido-mimetic of a Lewis antigen

<400> SEQUENCE: 23

Asp Leu Trp Met Trp Val Val Gly Lys Pro Ala Gly
1               5                   10

<210> SEQ ID NO 24
<211> LENGTH: 12
<212> TYPE: PRT
<213> ORGANISM: peptido-mimetic of a Lewis antigen

<400> SEQUENCE: 24

Asp Leu Trp Tyr Trp Val Val Gly Lys Pro Ala Gly
1               5                   10

<210> SEQ ID NO 25
<211> LENGTH: 12
<212> TYPE: PRT
<213> ORGANISM: peptido-mimetic of a Lewis antigen

<400> SEQUENCE: 25

Asp Leu Trp Asp His Val Val Gly Lys Pro Ala Gly
1               5                   10

<210> SEQ ID NO 26
<211> LENGTH: 12
<212> TYPE: PRT
<213> ORGANISM: peptido-mimetic of a Lewis antigen

<400> SEQUENCE: 26

Asp Leu Trp Asp Tyr Val Val Gly Lys Pro Ala Gly
1               5                   10

<210> SEQ ID NO 27
<211> LENGTH: 12
<212> TYPE: PRT
<213> ORGANISM: peptido-mimetic of a Lewis antigen

<400> SEQUENCE: 27

Asp Leu Trp Asp Met Val Val Gly Lys Pro Ala Gly
1               5                   10

<210> SEQ ID NO 28
<211> LENGTH: 12
<212> TYPE: PRT
<213> ORGANISM: peptido-mimetic of a Lewis antigen

<400> SEQUENCE: 28

Asp Leu Trp Asp Ala Val Val Gly Lys Pro Ala Gly
1               5                   10

<210> SEQ ID NO 29
<211> LENGTH: 12
<212> TYPE: PRT
```

-continued

<213> ORGANISM: peptido-mimetic of a Lewis antigen

<400> SEQUENCE: 29

Asp Leu Trp Asp Asp Val Val Gly Lys Pro Ala Gly
1               5                   10

<210> SEQ ID NO 30
<211> LENGTH: 12
<212> TYPE: PRT
<213> ORGANISM: peptido-mimetic of a Lewis antigen

<400> SEQUENCE: 30

Asp Leu Trp Asp Glu Val Val Gly Lys Pro Ala Gly
1               5                   10

<210> SEQ ID NO 31
<211> LENGTH: 12
<212> TYPE: PRT
<213> ORGANISM: peptido-mimetic of a Lewis antigen

<400> SEQUENCE: 31

Asp Leu Trp Asp Lys Val Val Gly Lys Pro Ala Gly
1               5                   10

<210> SEQ ID NO 32
<211> LENGTH: 12
<212> TYPE: PRT
<213> ORGANISM: peptido-mimetic of a Lewis antigen

<400> SEQUENCE: 32

Asp Leu Trp Asp Arg Val Val Gly Lys Pro Ala Gly
1               5                   10

<210> SEQ ID NO 33
<211> LENGTH: 12
<212> TYPE: PRT
<213> ORGANISM: peptido-mimetic of a Lewis antigen

<400> SEQUENCE: 33

Asp Leu Trp Asp Ser Val Val Gly Lys Pro Ala Gly
1               5                   10

<210> SEQ ID NO 34
<211> LENGTH: 12
<212> TYPE: PRT
<213> ORGANISM: peptido-mimetic of a Lewis antigen

<400> SEQUENCE: 34

Asp Leu Trp Asp Trp Leu Val Gly Lys Pro Ala Gly
1               5                   10

<210> SEQ ID NO 35
<211> LENGTH: 12
<212> TYPE: PRT
<213> ORGANISM: peptido-mimetic of a Lewis antigen

<400> SEQUENCE: 35

Asp Leu Trp Asp Trp Tyr Val Gly Lys Pro Ala Gly
1               5                   10

<210> SEQ ID NO 36
<211> LENGTH: 12
<212> TYPE: PRT
<213> ORGANISM: peptido-mimetic of a Lewis antigen -continued

```
<400> SEQUENCE: 36

Asp Leu Trp Asp Trp Ala Val Gly Lys Pro Ala Gly
1               5                   10

<210> SEQ ID NO 37
<211> LENGTH: 12
<212> TYPE: PRT
<213> ORGANISM: peptido-mimetic of a Lewis antigen

<400> SEQUENCE: 37

Asp Leu Trp Asp Trp Ser Val Gly Lys Pro Ala Gly
1               5                   10

<210> SEQ ID NO 38
<211> LENGTH: 12
<212> TYPE: PRT
<213> ORGANISM: peptido-mimetic of a Lewis antigen

<400> SEQUENCE: 38

Asp Leu Trp Asp Trp Val Leu Gly Lys Pro Ala Gly
1               5                   10

<210> SEQ ID NO 39
<211> LENGTH: 12
<212> TYPE: PRT
<213> ORGANISM: peptido-mimetic of a Lewis antigen

<400> SEQUENCE: 39

Asp Leu Trp Asp Trp Val Ala Gly Lys Pro Ala Gly
1               5                   10

<210> SEQ ID NO 40
<211> LENGTH: 12
<212> TYPE: PRT
<213> ORGANISM: peptido-mimetic of a Lewis antigen

<400> SEQUENCE: 40

Asp Leu Trp Asp Trp Val Asp Gly Lys Pro Ala Gly
1               5                   10

<210> SEQ ID NO 41
<211> LENGTH: 12
<212> TYPE: PRT
<213> ORGANISM: peptido-mimetic of a Lewis antigen

<400> SEQUENCE: 41

Asp Leu Trp Asp Trp Val Asp Cys Lys Pro Ala Gly
1               5                   10

<210> SEQ ID NO 42
<211> LENGTH: 12
<212> TYPE: PRT
<213> ORGANISM: peptido-mimetic of a Lewis antigen

<400> SEQUENCE: 42

Asp Leu Trp Asp Trp Val Asp Pro Lys Pro Ala Gly
1               5                   10

<210> SEQ ID NO 43
<211> LENGTH: 12
<212> TYPE: PRT
<213> ORGANISM: peptido-mimetic of a Lewis antigen

<400> SEQUENCE: 43
```

```
Asp Leu Trp Asp Trp Val Asp Asp Tyr Pro Ala Gly
1               5                   10
```

<210> SEQ ID NO 44
<211> LENGTH: 12
<212> TYPE: PRT
<213> ORGANISM: peptido-mimetic of a Lewis antigen

<400> SEQUENCE: 44

```
Asp Leu Trp Asp Trp Val Asp Asp Phe Pro Ala Gly
1               5                   10
```

<210> SEQ ID NO 45
<211> LENGTH: 4
<212> TYPE: PRT
<213> ORGANISM: peptido-mimetic of a Lewis antigen

<400> SEQUENCE: 45

```
Asp Leu His Glu
1
```

<210> SEQ ID NO 46
<211> LENGTH: 6
<212> TYPE: PRT
<213> ORGANISM: peptido-mimetic of a Lewis antigen

<400> SEQUENCE: 46

```
Asp Leu Trp Glu His Leu
1               5
```

<210> SEQ ID NO 47
<211> LENGTH: 12
<212> TYPE: PRT
<213> ORGANISM: peptido-mimetic of a Lewis antigen

<400> SEQUENCE: 47

```
Leu Asp Trp Glu Trp Val Val Gly Lys Pro Ala Gly
1               5                   10
```

<210> SEQ ID NO 48
<211> LENGTH: 4
<212> TYPE: PRT
<213> ORGANISM: peptido-mimetic of a Lewis antigen

<400> SEQUENCE: 48

```
Asp Leu Asp Leu
1
```

<210> SEQ ID NO 49
<211> LENGTH: 12
<212> TYPE: PRT
<213> ORGANISM: peptido-mimetic of a Lewis antigen

<400> SEQUENCE: 49

```
Glu Ile His Asp Trp Val Val Gly Lys Pro Ala Gly
1               5                   10
```

<210> SEQ ID NO 50
<211> LENGTH: 6
<212> TYPE: PRT
<213> ORGANISM: peptido-mimetic of a Lewis antigen

<400> SEQUENCE: 50

```
Asp Leu Trp Glu His Leu
1               5
```

```
<210> SEQ ID NO 51
<211> LENGTH: 12
<212> TYPE: PRT
<213> ORGANISM: peptido-mimetic of a Lewis antigen

<400> SEQUENCE: 51

Leu Asp Asp Asp Trp Val Val Gly Lys Pro Ala Gly
1               5                   10

<210> SEQ ID NO 52
<211> LENGTH: 12
<212> TYPE: PRT
<213> ORGANISM: peptido-mimetic of a Lewis antigen

<400> SEQUENCE: 52

Glu Ile His Glu Trp Val Val Gly Lys Pro Ala Gly
1               5                   10

<210> SEQ ID NO 53
<211> LENGTH: 8
<212> TYPE: PRT
<213> ORGANISM: peptido-mimetic of a Lewis antigen

<400> SEQUENCE: 53

Asp Leu Trp Asp His Leu Leu Ala
1               5

<210> SEQ ID NO 54
<211> LENGTH: 12
<212> TYPE: PRT
<213> ORGANISM: peptido-mimetic of a Lewis antigen

<400> SEQUENCE: 54

Leu Asp Asp Leu Trp Val Val Gly Lys Pro Ala Gly
1               5                   10

<210> SEQ ID NO 55
<211> LENGTH: 12
<212> TYPE: PRT
<213> ORGANISM: peptido-mimetic of a Lewis antigen

<400> SEQUENCE: 55

Glu Ile His Glu His Leu Val Gly Lys Pro Ala Gly
1               5                   10

<210> SEQ ID NO 56
<211> LENGTH: 10
<212> TYPE: PRT
<213> ORGANISM: peptido-mimetic of a Lewis antigen

<400> SEQUENCE: 56

Trp Asp Trp Val Val Gly Lys Pro Ala Gly
1               5                   10

<210> SEQ ID NO 57
<211> LENGTH: 9
<212> TYPE: PRT
<213> ORGANISM: peptido-mimetic of a Lewis antigen

<400> SEQUENCE: 57

Asp Trp Val Val Gly Lys Pro Ala Gly
1               5
```

```
<210> SEQ ID NO 58
<211> LENGTH: 8
<212> TYPE: PRT
<213> ORGANISM: peptido-mimetic of a Lewis antigen

<400> SEQUENCE: 58

Trp Val Val Gly Lys Pro Ala Gly
1               5

<210> SEQ ID NO 59
<211> LENGTH: 7
<212> TYPE: PRT
<213> ORGANISM: peptido-mimetic of a Lewis antigen

<400> SEQUENCE: 59

Val Val Gly Lys Pro Ala Gly
1               5

<210> SEQ ID NO 60
<211> LENGTH: 6
<212> TYPE: PRT
<213> ORGANISM: peptido-mimetic of a Lewis antigen

<400> SEQUENCE: 60

Val Gly Lys Pro Ala Gly
1               5

<210> SEQ ID NO 61
<211> LENGTH: 5
<212> TYPE: PRT
<213> ORGANISM: peptido-mimetic of a Lewis antigen

<400> SEQUENCE: 61

Gly Lys Pro Ala Gly
1               5

<210> SEQ ID NO 62
<211> LENGTH: 4
<212> TYPE: PRT
<213> ORGANISM: peptido-mimetic of a Lewis antigen

<400> SEQUENCE: 62

Lys Pro Ala Gly
1

<210> SEQ ID NO 63
<211> LENGTH: 12
<212> TYPE: PRT
<213> ORGANISM: peptido-mimetic of a Lewis antigen

<400> SEQUENCE: 63

Asp Leu Trp Asp Phe Val Val Gly Lys Pro Ala Gly
1               5                   10

<210> SEQ ID NO 64
<211> LENGTH: 12
<212> TYPE: PRT
<213> ORGANISM: peptido-mimetic of a Lewis antigen

<400> SEQUENCE: 64

Asp Leu Trp Asp Trp Val Ile Gly Lys Pro Ala Gly
1               5                   10

<210> SEQ ID NO 65
<211> LENGTH: 12
```

-continued

<212> TYPE: PRT
<213> ORGANISM: peptido-mimetic of a Lewis antigen

<400> SEQUENCE: 65

Asp Leu Trp Asp Trp Val Val Ala Lys Pro Ala Gly
1               5                   10

<210> SEQ ID NO 66
<211> LENGTH: 12
<212> TYPE: PRT
<213> ORGANISM: peptido-mimetic of a Lewis antigen

<400> SEQUENCE: 66

Asp Leu Trp Asp Trp Val Val Ser Lys Pro Ala Gly
1               5                   10

<210> SEQ ID NO 67
<211> LENGTH: 12
<212> TYPE: PRT
<213> ORGANISM: peptido-mimetic of a Lewis antigen

<400> SEQUENCE: 67

Asp Leu Trp Asp Trp Val Val Glu Lys Pro Ala Gly
1               5                   10

<210> SEQ ID NO 68
<211> LENGTH: 12
<212> TYPE: PRT
<213> ORGANISM: peptido-mimetic of a Lewis antigen

<400> SEQUENCE: 68

Asp Leu Trp Asp Trp Val Val Asp Lys Pro Ala Gly
1               5                   10

<210> SEQ ID NO 69
<211> LENGTH: 12
<212> TYPE: PRT
<213> ORGANISM: peptido-mimetic of a Lewis antigen

<400> SEQUENCE: 69

Asp Leu Trp Asp Trp Val Val Gly Glu Pro Ala Gly
1               5                   10

<210> SEQ ID NO 70
<211> LENGTH: 12
<212> TYPE: PRT
<213> ORGANISM: peptido-mimetic of a Lewis antigen

<400> SEQUENCE: 70

Asp Leu Trp Asp Trp Val Val Gly Asp Pro Ala Gly
1               5                   10

<210> SEQ ID NO 71
<211> LENGTH: 12
<212> TYPE: PRT
<213> ORGANISM: peptido-mimetic of a Lewis antigen

<400> SEQUENCE: 71

Asp Leu Trp Asp Trp Val Val Gly Lys Glu Ala Gly
1               5                   10

<210> SEQ ID NO 72
<211> LENGTH: 12
<212> TYPE: PRT
<213> ORGANISM: peptido-mimetic of a Lewis antigen

```
<400> SEQUENCE: 72

Asp Leu Trp Asp Trp Val Val Gly Lys Asp Ala Gly
1               5                   10

<210> SEQ ID NO 73
<211> LENGTH: 12
<212> TYPE: PRT
<213> ORGANISM: peptido-mimetic of a Lewis antigen

<400> SEQUENCE: 73

Asp Leu Trp Asp Trp Val Val Gly Lys Pro Asp Gly
1               5                   10

<210> SEQ ID NO 74
<211> LENGTH: 12
<212> TYPE: PRT
<213> ORGANISM: peptido-mimetic of a Lewis antigen

<400> SEQUENCE: 74

Asp Leu Trp Asp Trp Val Val Gly Lys Pro Ala Asp
1               5                   10

<210> SEQ ID NO 75
<211> LENGTH: 12
<212> TYPE: PRT
<213> ORGANISM: peptido-mimetic of a Lewis antigen

<400> SEQUENCE: 75

Asp Leu Trp Asp Trp Val Lys Glu Lys Pro Ala Gly
1               5                   10

<210> SEQ ID NO 76
<211> LENGTH: 12
<212> TYPE: PRT
<213> ORGANISM: peptido-mimetic of a Lewis antigen

<400> SEQUENCE: 76

Asp Leu Trp Asp Trp Val Leu Ala Lys Pro Ala Gly
1               5                   10

<210> SEQ ID NO 77
<211> LENGTH: 12
<212> TYPE: PRT
<213> ORGANISM: peptido-mimetic of a Lewis antigen

<400> SEQUENCE: 77

Asp Leu Trp Asp Trp Val Val Gly Glu Asp Ala Gly
1               5                   10

<210> SEQ ID NO 78
<211> LENGTH: 12
<212> TYPE: PRT
<213> ORGANISM: peptido-mimetic of a Lewis antigen

<400> SEQUENCE: 78

Asp Leu Trp Asp Trp Val Val Gly Lys Pro Glu Lys
1               5                   10

<210> SEQ ID NO 79
<211> LENGTH: 12
<212> TYPE: PRT
<213> ORGANISM: peptido-mimetic of a Lewis antigen

<400> SEQUENCE: 79
```

```
Asp Leu Trp Asp Trp Val Lys Glu Glu Pro Ala Gly
1               5                   10
```

<210> SEQ ID NO 80
<211> LENGTH: 12
<212> TYPE: PRT
<213> ORGANISM: peptido-mimetic of a Lewis antigen

<400> SEQUENCE: 80

```
Asp Leu Trp Asp Trp Val Val Gly Lys Asp Glu Lys
1               5                   10
```

<210> SEQ ID NO 81
<211> LENGTH: 12
<212> TYPE: PRT
<213> ORGANISM: peptido-mimetic of a Lewis antigen

<400> SEQUENCE: 81

```
Asp Leu Trp Asp Trp Val Val Gly Glu Asp Glu Lys
1               5                   10
```

<210> SEQ ID NO 82
<211> LENGTH: 12
<212> TYPE: PRT
<213> ORGANISM: peptido-mimetic of a Lewis antigen

<400> SEQUENCE: 82

```
Asp Leu Trp Asp Trp Val Lys Glu Gly Asp Glu Lys
1               5                   10
```

<210> SEQ ID NO 83
<211> LENGTH: 8
<212> TYPE: PRT
<213> ORGANISM: peptido-mimetic of a Lewis antigen

<400> SEQUENCE: 83

```
Ala Pro Trp Leu Tyr Ala Gly Pro
1               5
```

<210> SEQ ID NO 84
<211> LENGTH: 12
<212> TYPE: PRT
<213> ORGANISM: peptido-mimetic of a Lewis antigen

<400> SEQUENCE: 84

```
Ala Ser Ala Val Asn Leu Tyr Ile Pro Thr Gln Glu
1               5                   10
```

<210> SEQ ID NO 85
<211> LENGTH: 12
<212> TYPE: PRT
<213> ORGANISM: peptido-mimetic of a Lewis antigen

<400> SEQUENCE: 85

```
Val Tyr Leu Ala Pro Gly Arg Ile Ser Arg Asp Tyr
1               5                   10
```

<210> SEQ ID NO 86
<211> LENGTH: 12
<212> TYPE: PRT
<213> ORGANISM: peptido-mimetic of a Lewis antigen

<400> SEQUENCE: 86

```
Val Tyr Leu Ala Pro Gly Arg Phe Ser Arg Asp Tyr
```

-continued

<210> SEQ ID NO 87
<211> LENGTH: 12
<212> TYPE: PRT
<213> ORGANISM: peptido-mimetic of a Lewis antigen

<400> SEQUENCE: 87

Cys Thr Ser His Trp Gly Val Leu Ser Gln Arg Arg
1               5                   10

<210> SEQ ID NO 88
<211> LENGTH: 12
<212> TYPE: PRT
<213> ORGANISM: peptido-mimetic of a Lewis antigen

<400> SEQUENCE: 88

Arg Val Leu Ser Pro Glu Ser Tyr Leu Gly Pro Ser
1               5                   10

<210> SEQ ID NO 89
<211> LENGTH: 12
<212> TYPE: PRT
<213> ORGANISM: peptido-mimetic of a Lewis antigen

<400> SEQUENCE: 89

Arg Val Leu Ser Pro Glu Ser Tyr Leu Gly Pro Ala
1               5                   10

<210> SEQ ID NO 90
<211> LENGTH: 11
<212> TYPE: PRT
<213> ORGANISM: peptido-mimetic of a Lewis antigen

<400> SEQUENCE: 90

Val Gly Asn Gly Val Leu Met Gly Arg Arg Gly
1               5                   10

<210> SEQ ID NO 91
<211> LENGTH: 12
<212> TYPE: PRT
<213> ORGANISM: peptido-mimetic of a Lewis antigen

<400> SEQUENCE: 91

Ser Thr Gly Leu Met Val Asp Phe Leu Glu Pro Gly
1               5                   10

<210> SEQ ID NO 92
<211> LENGTH: 12
<212> TYPE: PRT
<213> ORGANISM: peptido-mimetic of a Lewis antigen

<400> SEQUENCE: 92

Arg Val Leu Ser Pro Glu Ser Tyr Leu Gly Pro Ala
1               5                   10

<210> SEQ ID NO 93
<211> LENGTH: 12
<212> TYPE: PRT
<213> ORGANISM: peptido-mimetic of a Lewis antigen

<400> SEQUENCE: 93

Gly Asn Cys Arg Tyr Ile Gly Leu Arg Gln Phe Gly
1               5                   10

```
<210> SEQ ID NO 94
<211> LENGTH: 12
<212> TYPE: PRT
<213> ORGANISM: peptido-mimetic of a Lewis antigen

<400> SEQUENCE: 94

Asp Ile Arg Val Glu Pro Gly Gly Gly Tyr Thr His
1               5                   10

<210> SEQ ID NO 95
<211> LENGTH: 12
<212> TYPE: PRT
<213> ORGANISM: peptido-mimetic of a Lewis antigen

<400> SEQUENCE: 95

Ala Lys Thr Phe Gly Leu Glu His Gly Cys Glu Ala
1               5                   10

<210> SEQ ID NO 96
<211> LENGTH: 12
<212> TYPE: PRT
<213> ORGANISM: peptido-mimetic of a Lewis antigen

<400> SEQUENCE: 96

Ala Pro Ile His Thr Tyr Thr Gly Arg Ala Arg Gly
1               5                   10

<210> SEQ ID NO 97
<211> LENGTH: 13
<212> TYPE: PRT
<213> ORGANISM: peptido-mimetic of a Lewis antigen

<400> SEQUENCE: 97

Arg His Thr Cys Val Arg Ser Cys Cys Gly His Asp Arg
1               5                   10

<210> SEQ ID NO 98
<211> LENGTH: 12
<212> TYPE: PRT
<213> ORGANISM: peptido-mimetic of a Lewis antigen

<400> SEQUENCE: 98

Thr Lys Arg Pro Asp Leu Ile Val Asp Pro Ile Pro
1               5                   10

<210> SEQ ID NO 99
<211> LENGTH: 12
<212> TYPE: PRT
<213> ORGANISM: peptido-mimetic of a Lewis antigen

<400> SEQUENCE: 99

Asp Glu Val Arg Pro Asp Leu Ile Ser Thr Glu Glu
1               5                   10

<210> SEQ ID NO 100
<211> LENGTH: 12
<212> TYPE: PRT
<213> ORGANISM: peptido-mimetic of a Lewis antigen
<220> FEATURE:
<221> NAME/KEY: MISC_FEATURE
<222> LOCATION: (8)..(8)
<223> OTHER INFORMATION: Xaa in position 8 can be any amino acid

<400> SEQUENCE: 100

Asn Leu Arg Pro Lys Tyr Ile Xaa Leu Asp Ala Asp
```

```
                 1               5                    10

<210> SEQ ID NO 101
<211> LENGTH: 12
<212> TYPE: PRT
<213> ORGANISM: peptido-mimetic of a Lewis antigen

<400> SEQUENCE: 101

Thr Leu Ile Ala Phe Ala Asp Leu Val Asp Val Ile
1               5                   10

<210> SEQ ID NO 102
<211> LENGTH: 12
<212> TYPE: PRT
<213> ORGANISM: peptido-mimetic of a Lewis antigen

<400> SEQUENCE: 102

Val Gly Ile Trp Ser Val Val Ser Glu Gly Ser Arg
1               5                   10

<210> SEQ ID NO 103
<211> LENGTH: 12
<212> TYPE: PRT
<213> ORGANISM: peptido-mimetic of a Lewis antigen

<400> SEQUENCE: 103

Arg Cys Ser Val Gly Val Pro Phe Thr Met Glu Ser
1               5                   10

<210> SEQ ID NO 104
<211> LENGTH: 12
<212> TYPE: PRT
<213> ORGANISM: peptido-mimetic of a Lewis antigen

<400> SEQUENCE: 104

Gln Asp Gly Val Trp Glu His Val Leu Glu Gly Gly
1               5                   10

<210> SEQ ID NO 105
<211> LENGTH: 12
<212> TYPE: PRT
<213> ORGANISM: peptido-mimetic of a Lewis antigen

<400> SEQUENCE: 105

Val Glu Leu Ser Gly Arg Gly Gly Leu Cys Thr Trp
1               5                   10

<210> SEQ ID NO 106
<211> LENGTH: 12
<212> TYPE: PRT
<213> ORGANISM: peptido-mimetic of a Lewis antigen

<400> SEQUENCE: 106

Val Ile Gly Ala Ala Ser His Asp Glu Asp Val Asp
1               5                   10

<210> SEQ ID NO 107
<211> LENGTH: 12
<212> TYPE: PRT
<213> ORGANISM: peptido-mimetic of a Lewis antigen

<400> SEQUENCE: 107

Thr Ile Glu Pro Val Leu Ala Glu Met Phe Met Gly
1               5                   10
```

```
<210> SEQ ID NO 108
<211> LENGTH: 12
<212> TYPE: PRT
<213> ORGANISM: peptido-mimetic of a Lewis antigen

<400> SEQUENCE: 108

Asp Lys Glu Thr Phe Glu Leu Gly Leu Phe Asp Arg
1               5                   10

<210> SEQ ID NO 109
<211> LENGTH: 12
<212> TYPE: PRT
<213> ORGANISM: peptido-mimetic of a Lewis antigen

<400> SEQUENCE: 109

Phe Ser Gly Val Arg Gly Val Tyr Glu Ser Arg Thr
1               5                   10

<210> SEQ ID NO 110
<211> LENGTH: 12
<212> TYPE: PRT
<213> ORGANISM: peptido-mimetic of a Lewis antigen

<400> SEQUENCE: 110

Pro Asp Asp Ala Pro Met His Ser Thr Arg Val Glu
1               5                   10

<210> SEQ ID NO 111
<211> LENGTH: 9
<212> TYPE: PRT
<213> ORGANISM: peptido-mimetic of a Lewis antigen
<220> FEATURE:
<221> NAME/KEY: MISC_FEATURE
<222> LOCATION: (2)..(2)
<223> OTHER INFORMATION: Xaa in position 2 can be any amino acid
<221> NAME/KEY: MISC_FEATURE
<222> LOCATION: (4)..(4)
<223> OTHER INFORMATION: Xaa in position 4 can be any amino acid
<221> NAME/KEY: MISC_FEATURE
<222> LOCATION: (5)..(5)
<223> OTHER INFORMATION: Xaa in position 5 can be any amino acid

<400> SEQUENCE: 111

Gly Xaa Trp Xaa Xaa Val Leu Glu Gly
1               5

<210> SEQ ID NO 112
<211> LENGTH: 5
<212> TYPE: PRT
<213> ORGANISM: peptido-mimetic of a Lewis antigen
<220> FEATURE:
<221> NAME/KEY: MISC_FEATURE
<222> LOCATION: (4)..(4)
<223> OTHER INFORMATION: Xaa in position 4 can be any amino acid

<400> SEQUENCE: 112

Val Val Gly Xaa Pro
1               5

<210> SEQ ID NO 113
<211> LENGTH: 4
<212> TYPE: PRT
<213> ORGANISM: peptido-mimetic of a Lewis antigen

<400> SEQUENCE: 113

Arg Pro Asp Leu
1
```

<210> SEQ ID NO 114
<211> LENGTH: 5
<212> TYPE: PRT
<213> ORGANISM: peptido-mimetic of a Lewis antigen

<400> SEQUENCE: 114

Phe Ser Leu Leu Trp
1               5

<210> SEQ ID NO 115
<211> LENGTH: 12
<212> TYPE: PRT
<213> ORGANISM: peptido-mimetic of a Lewis antigen

<400> SEQUENCE: 115

Gly Gly Thr Val Glu Val Trp Ser Ile Lys Gly Gly
1               5                   10

<210> SEQ ID NO 116
<211> LENGTH: 12
<212> TYPE: PRT
<213> ORGANISM: peptido-mimetic of a Lewis antigen

<400> SEQUENCE: 116

Asp His Phe Ser Gln Ala Gly Ser Ser Asn His His
1               5                   10

<210> SEQ ID NO 117
<211> LENGTH: 12
<212> TYPE: PRT
<213> ORGANISM: peptido-mimetic of a Lewis antigen

<400> SEQUENCE: 117

Asp Asp Pro Val Thr Pro Val Ile Asp Phe Gly Lys
1               5                   10

<210> SEQ ID NO 118
<211> LENGTH: 12
<212> TYPE: PRT
<213> ORGANISM: peptido-mimetic of a Lewis antigen

<400> SEQUENCE: 118

Arg Asp Gly Leu Ile Asp Phe Val Val Ala Gly Thr
1               5                   10

<210> SEQ ID NO 119
<211> LENGTH: 15
<212> TYPE: PRT
<213> ORGANISM: peptido-mimetic of a Lewis antigen

<400> SEQUENCE: 119

Gly Leu Asp Leu Leu Gly Asp Val Arg Ile Pro Val Val Arg Arg
1               5                   10                  15

<210> SEQ ID NO 120
<211> LENGTH: 15
<212> TYPE: PRT
<213> ORGANISM: peptido-mimetic of a Lewis antigen

<400> SEQUENCE: 120

Val Gly Ile Thr Gly Phe Val Asp Pro Leu Pro Leu Arg Leu Leu
1               5                   10                  15

```
<210> SEQ ID NO 121
<211> LENGTH: 8
<212> TYPE: PRT
<213> ORGANISM: peptido-mimetic of a Lewis antigen

<400> SEQUENCE: 121

Ala Pro Trp Leu Tyr Gly Pro Ala
1               5
```

COMPOSITIONS AND METHODS FOR TREATMENT OF CANCER

CROSS-REFERENCE TO RELATED APPLICATIONS

This is a 371 of PCT/US99/26277, which claims the benefit of the priority of U.S. patent application No. 60/107,478, filed Nov. 6, 1998.

This invention was supported in part by funds from the U.S. Government (United States Army Grant DAMD 17-96-1-6232 and NIH Grant No. AI45133). The U.S. Government may therefore have certain rights in the invention.

FIELD OF THE INVENTION

The invention relates generally to animal cell adhesion, and more specifically to peptido-mimetics of carbohydrate ligands of animal cell adhesion proteins and methods of using the same.

BACKGROUND OF THE INVENTION

Tumor metastasis is a multistep process requiring detachment of malignant cells from the primary tumor, penetration of blood or lymph vessels and attachment to endothelium of distant organs and formation of new tumors. The ability of disseminating cancer cells to establish metastases in secondary organs is regulated by a combination of factors, including access to the organ microvasculature and specific host-tumor interactions [Radinsky and Fidler, 1992, *In Vivo* 6:325–331]. Hematogenous dissemination brings cancer cells into contact with leukocytes, platelets, and endothelium [Nicolson, 1989, *Curr. Opin. Cell. Biol.* 1:1009–1019, Bevilaqua et al., 1989, *Science* 243:1160–1165]. The attachment of circulating tumor cells to the vascular endothelium of the target organ is thought to be a key step in the metastatic cascade. Once tumor cells adhere to endothelial cells (EC), they penetrate through the EC layer, moving into subendothelial tissues where metastasis is established.

Studies of leukocyte transmigration have suggested that the specificity of the interaction between circulating lymphocytes and the microvascular endothelium may be determined by the outcome of a series of sequential adhesion molecule-ligand interactions involving complex carbohydrate structures on the surface of leukocytes and adhesion molecules on the surface of endothelial cells. It appears likely that the process of tumor extravasation is mediated through a series of analogous adhesive interactions [Brodt, 1996, In: *Cell adhesion and invasion in cancer metastasis*, vol. 21 pp. 167–242, Brodt, ed., Landes, Austin and Springer-Verlag, Berlin].

Prominent among the vascular endothelial cell adhesion molecules implicated in both leukocyte and tumor cell transmigration are members of the selectin family. This family of adhesion molecules supports the adhesion of leukocytes to the vessel wall through the recognition of specific carbohydrate structures and thereby mediates critical cell-cell interactions in processes such as leukocyte trafficking, thrombosis, acute and chronic inflammation and ischemia reperfusion injury [Bucher and Picker, 1996, *Science* 272:60–66; Lasky, 1995, *Annu. Rev. Biochem.* 64:113–139; Varki, 1994, *Proc. Natl. Acad. Sci. USA* 91:7390–7397; Bevilaqua and Nelson, 1993, *J. Clin. Invest.* 91:379–387]. Selectins recognize and bind specific carbohydrate antigens expressed on tumor cell surfaces and mediate the initial interaction between tumor cells and endothelium [Mannori et al., 1995, *Cancer. Res.* 55:4425–4431 (Mannori I)].

Selectins are subdivided into E-, L-, and P-selectin subgroups. Inflammatory mediators such as tumor necrosis factor α (TNF-α) and interleukin 1β (IL-1β) induce vascular endothelium to express E- and P-selectin. E-selectin is a calcium-dependent molecule expressed by activated vascular endothelium during the process of leucocyte recruitment. E-selectin binds to glycoconjugates carrying a terminal tetrasaccharide Lewis (Le) antigen, sialyl-LeX (SA-LeX), [NeuAcα2,3Galα1β1,4(Fucα1,3) GlcNAcβ1,3Galβ1,4Glcβ1-R], but displays higher affinity for the SA-Le$^a$ structure ([NeuAcα2,3Galβ1,3(Fucα1,4) GlcNAcβ1,3Galβ1,4Glcβ1-R], a positional isomer of SA-LeX.

P-selectin is expressed by activated platelets and endothelial cells. P-selectin has been shown to mediate adhesive interactions of some colon adenocarcinoma cells with thrombin-activated platelets [Mannori I, cited above]. During metastatic dissemination, tumor-platelet adhesion may result in the formation of neoplastic emboli that facilitate the arrest of tumor cells in the microvasculature of organs [Karpatkin and Pearlstein, 1981, *Ann. Intern. Med.* 95: 636–641].

L-selectin is constitutively expressed by a majority of leukocytes, including neutrophils, monocytes, natural killer cells and most lymphocytes. L-selectin expressed on leukocytes can support interaction with cancer cells, enhancing metastatic potential [Welch et al., 1989, *Proc. Natl. Acad. Sci. USA* 86:5859–5863]. Other studies demonstrate that the engagement of L-selectin on lymphocytes can stimulate their anti-tumor cell cytotoxic activity [Seth et al., 1991, *Proc. Natl. Acad. Sci. USA* 88: 7877–7881].

Selectin recognition of carbohydrate ligands involves primarily the N-terminal of C-type lectin domain, influenced by the EGF-like domain, and to a lesser degree the short consensus repeats [Kolbinger et al., 1988, *Biochemistry* 35:6385–6392; Revelle et al., 1996, *J. Biol. Chem.* 271:16160–16170; Li et al., 1994, *J. Biol. Chem.* 269:4431–4437]. Mutagenesis studies of the lectin domain of the selectins [Erbe et al., 1993, *J. Cell. Biol.* 120:1227–1235] and the crystal structure of the E-selectin lectin plus EGF-like domain solved at 2.0 Å resolution [Graves et al., 1994, *Nature* 367:532–538] have identified a number of positively charged residues involved in the binding to the SA-LeX carbohydrate ligand. Most of these residues are identical in all selectins and they are likely to recognize essential carbohydrate moieties such as sialic acid and fucose of SA-LeX. The identified residues are derived from noncontiguous sequences at both the N- and C-terminus of the lectin domain.

Although adhesion pathways utilized by different tumors exhibit considerable diversity, metastasis apparently involves the interaction of at least one member of the selectin family of adhesion molecules with the antigens SA-Le$^a$ and/or SA-LeX. These ligands may be involved in tumor metastasis by mediating binding of blood-borne tumor cells via E- and/or P-selectin to vascular endothelium [Giavazzi et al., 1993, *J. Clin. Invest.* 92:3038–3044; Dejana et al., 1992, *Lab. Invest.* 66:324–3130, Takada et al., 1993, *Cancer. Res.* 53:354–361; Sawada et al., 1994, *J. Biol. Chem.* 269:1425–1431]. Cancer cells that express both SA-Le$^a$ and SA-LeX undergo SA-Le$^a$-mediated adhesion almost exclusively, possibly due to the higher affinity for the SA-Le$^a$ structure, or differential presentation of this oligosaccharide determinant. Thus, SA-Le$^a$ might play a major role as a ligand in the E-selectin dependent adhesion to EC in vivo. Indeed, SA-Lea specific monoclonal antibodies (MAbs) were inhibitory for adhesion of colon carcinoma cells to human umbilical cord vein endothelial cells (HUVEC).

In vivo studies have provided further evidence of the potential importance of the carbohydrate ligand/E-selectin interaction in tumor metastasis [Brodt et al., 1997, *Int. J. Cancer* 71:612–619; Mannori et al., 1997, *Am. J. Pathol.* 151:233–243 (Mannori II), Biancone et al., 1996, *J. Exp. Med.* 183:581–587].

Alternatively, some carcinoma cells do not express these carbohydrate determinants (i.e., SA-LeX and SA-Le$^a$) and yet they can attach to EC prior to activation. Further, this adhesion is not augmented by cytokine treatment, suggesting E-selectin-independent adhesion [Iwai et al., 1993, *Int. J. Cancer* 54:972–977, Tozeren et al., 1995, *Int. J. Cancer* 60:426–431; Miyake et al., 1992, *New Eng. J. Med.* 327:14–18; Garrigues et al., 1992, *J. Cell. Biol.* 125:129–142].

Studies have also demonstrated the role of oligosaccharides in inflammatory responses. Neutrophil extravasation is enabled by a multistep process initiated by the selectin family [Kansas, 1996, *Blood* 88: 3259–3287]. Neutrophil-endothelial cell interaction mediated via the selectins in the context of vascular shear flow, are characterized by transient tethering of the neutrophils, followed by rolling of the neutrophil along the endothelial surface of the vessel wall. Studies in vivo and in vitro indicate that selectin-dependent neutrophil rolling is essential to subsequent events in the transmigration process. Neutrophils are exposed to endothelial cell derived IL-8, platelet-activating factor and other neutrophil-activating molecules [Lowe, 1997, In: *The selectins: Inhibitors of leukocyte endothelial adhesion*, pp. 143–177, Vestweber, ed., Harwood Academic Publishers, Reading, UK], which in turn promote activation of neutrophil P2 integrins, leading to integrin-dependent firm adhesion to the integrin receptor ICAM-1, and finally to neutrophil extravasation, possibly via homophilic interaction of platelet/endothelial cell adhesion molecule 1.

The expression of ligands for selectins, particularly E-selectin, by both neutrophils and carcinoma cells raises the possibility that metastases are equivalent to the inflammatory process in which tumor cells, particularly carcinoma cells, use the same molecular mechanism(s) for cancer cell-EC interaction as lymphocytes, through the adhesion interaction of the endothelial cell selectins with the tumor-associated carbohydrate ligands, e.g., SA-LeX, SA-Le$^a$, and LeY.

In addition to their role in cell adhesion, carbohydrate structures also play a role in angiogenesis. Aberrant angiogenesis can occur in a variety of pathologic conditions. Neovascularization of tumors occurs by aberrant stimulation of normally quiescent endothelial cells to migrate, proliferate and form new capillary blood vessels [Ingber and Folkman, 1989, *J. Cell. Biol.* 109:3317–3330]. The experimental evidence suggests that E-selectin and its ligand SA-LeX function in angiogenesis [Nguyen et al., 1982, *J. Biol. Chem.* 267:26157–26165]. Thus, proliferating microvascular endothelium presents a potential target for anti-cancer and anti-angiogenic therapies through the inhibition of E-selectin-dependent carbohydrate-mediated interactions [Folkman, 1995, *N. Engl. J. Med.* 333:1757–1763].

Although recent studies suggest the importance of carbohydrate ligand-cell adhesion interactions in tumor metastasis, angiogenesis and inflammatory responses, the complex nature of the carbohydrate ligands involved has long hampered studies of these processes. The difficult chemical or enzymatic synthesis required by these complex carbohydrate ligands and the technical complexity involved in analyzing the functional/structural interactions of these ligands with selectins at the molecular level have severely hindered the development of anti-adhesion therapeutics for treatment of these disease processes for which there is no effective treatment.

Many peptide mimics of carbohydrate structures have been described in the literature [see, e.g., Agadjanyan, M. et al, 1997, *Nature Biotechnol.* 15: 547–551, among others] including those binding with high affinity to E-selectin [Tsukida, T. et al, 1998, *J. Med. Chem.* 41: 4279–4287]. A peptide that mimics the GD1 ganglioside, also involved in cell adhesion and metastasis of melanoma cells, has been recently described [Ishikawa, D. et al, 1998, *FEBS Lett.* 441: 20–24]. This peptide isolated from a peptide phage display library using an anti-GD1 antibody inhibits metastasis in an in vivo model.

Thus, there remains a long-felt and acute need for the development of techniques and probes for the study of complex carbohydrate ligand-cell adhesion molecule interactions, and for the development of anti-tumor, anti-inflammatory and angiogenesis-blocking therapeutics based on the selective inhibition of these interactions.

SUMMARY OF THE INVENTION

The present invention meets the above-stated needs by providing novel peptido-mimetics of carbohydrate structures and uses therefor in affecting animal cell adhesion mediated by carbohydrate ligand-cellular lectin protein receptor interactions.

In one aspect, the invention includes a composition comprising a peptido-mimetic of a carbohydrate ligand of an adhesion molecule in a physiologically acceptable carrier. In one embodiment, the adhesion molecule is a selectin, particularly E-selectin. In another embodiment, the ligand is a Lewis antigen. Particularly desirable are peptidomimetics of the Lewis antigens SA-Le$^a$, SA-LeX, and LeY. A variety of specific peptido-mimetics are recited in the detailed disclosure such peptido-mimetics may be modified as described herein.

In still another aspect, the invention provides a method of modulating binding of an adhesion molecule to a carbohydrate ligand. The method comprises contacting the adhesion molecule (e.g., a selectin) with a peptido-mimetic of the carbohydrate ligand, so that binding of the adhesion molecule to the carbohydrate ligand is modified or altered in a therapeutically effective manner.

In a further aspect, the invention provides a method of modulating adhesion of a tumor cell to an adhesion molecule located on an endothelial cell. The method comprises contacting the tumor cell with a peptido-mimetic of a carbohydrate ligand. The peptido-mimetic modulates adhesion of the tumor cell to the endothelial cell. The adhesion molecule may be, e.g., a selectin. The ligand is preferably a Lewis antigen.

In still another aspect, the invention provides a method of treating cancer in a mammal by administering an effective amount of a peptido-mimetic of a carbohydrate ligand to the mammal. The ligand is preferably a Lewis antigen. Administration of the peptido-mimetic reduces adhesion of tumor cells to endothelial cells in the mammal, thereby reducing metastasis of the cancer.

In yet a further aspect, the invention provides a method of inhibiting an inflammatory response in a mammal by contacting an endothelial cell with an effective amount of a peptido-mimetic of a carbohydrate ligand. The ligand is preferably a Lewis antigen. The specific peptido-mimetics described herein can be used in this method.

As another aspect, the invention provides additional methods of identifying a variety of peptido-mimetics of carbohydrate ligands. The peptido-mimetics inhibit the normal binding between the ligand and its natural binding partner. In one embodiment, the binding partner is an adhesion molecule, such as a selectin. In another embodiment, carbohydrate ligand is located on the surface of a tumor cell and is a Lewis antigen. In a further embodiment of this method, the carbohydrate ligand is located on the surface of a tumor cell and it normally binds to an adhesion molecule on human umbilical cord vein endothelial cells (HUVEC). In another embodiment, the carbohydrate ligand affects capillary tube formation or angiogenesis. In still another embodiment, the peptido-mimetic affects adhesion of a selected cell, e.g., a neutrophil or tumor cell, to an adhesion molecule located on an endothelial cell. In another embodiment, the carbohydrate ligand affects neutrophil recruitment. The steps of these methods are described in detail below.

In yet another aspect, the invention provides a method of producing peptido-mimetics of Lewis antigens, particularly peptido-mimetics not including APWLYAGP [SEQ ID NO: 83]. This method comprises the steps of screening a random peptide library, in which the peptides are expressed as fusion proteins on the surface of bacterial clones, with antibodies specific for the Lewis antigens and/or an E-selectin immunoglobulin fusion protein; and selecting clones which bind the antibodies and/or the fusion protein. The selected clones produce peptido-mimetics of the Lewis antigens.

Other aspects and advantages of the present invention are described further in the following detailed description of the preferred embodiments thereof.

DETAILED DESCRIPTION OF THE INVENTION

Figure 1A:
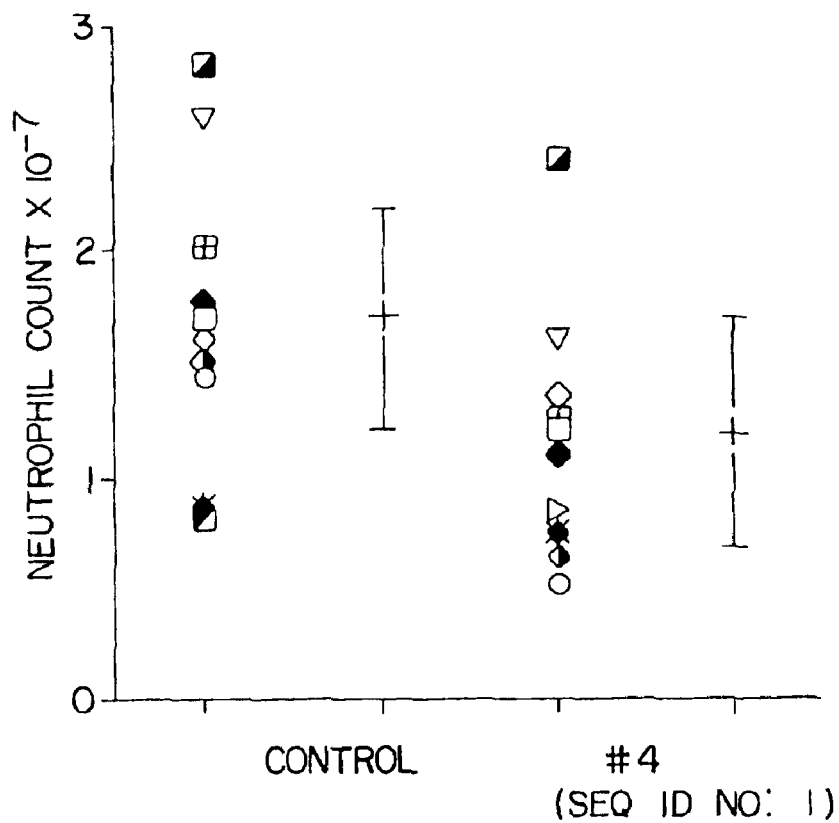
FIG. 1A is a diagram depicting the reduction of neutrophil influx upon administration of DLWDWVVGKPAG [SEQ ID NO: 1] mimicking SA-Le$^a$ carbohydrate in mice with chemically induced peritonitis. The neutrophil count results were obtained from four experiments (three mice in each group). Unrelated peptide was administered in control mice. Statistical analysis of the data using nonparametric unpaired t-test yielded P values <0.001 for the data shown in FIG. 1A.

The invention is based on the discovery that peptido-mimetics of complex carbohydrate structures block adhesion of tumor cells and leukocytes to endothelial cells. The production of small peptide molecules which mimic complex carbohydrate structures are useful for blocking carbohydrate ligand-cell adhesion molecule interactions involved in metastasis, angiogenesis, and inflammatory responses. Thus, these peptido-mimetics are useful as anti-adhesion therapeutics. The evaluation of complex carbohydrate ligand-adhesion molecule interactions at the molecular level enables the design of peptido-mimetics and possibly other compounds which block these adhesion interactions thereby disrupting the disease processes mediated by them. Further, the ability to generate peptide mimotopes of complex carbohydrate structures enables the use of recombinant peptide library display technology in discovering novel blocking agents for important therapeutic targets which bind carbohydrate ligands. The compositions and methods of this invention are also useful in designing additional therapeutics to inhibit the adhesion interactions required for disease processes.

As used herein, the term "peptido-mimetic" means a peptide or polypeptide that mimics complex carbohydrate conformations and structures. A subset of peptido-mimetics are referred to as "mimotopes". Mimotopes are small peptido-mimetics, generally from 7 to about 15 amino acids in length which mimic complex carbohydrate structures, including the carbohydrate ligands for endothelial adhesion molecules. Mimotypes are also capable of blocking the ligand-adhesion molecule interaction. Throughout this specification, these term are used interchangeably. These small peptides also facilitate the study of complex structural/ conformational relationships between these ligands and cellular lectins.

A. Peptides of the Invention

A composition of this invention comprises at least one peptido-mimetic of a carbohydrate ligand of an adhesion molecule in a physiologically acceptable carrier. In one embodiment, the adhesion molecule is a selectin, such as E-selectin. In another embodiment, the ligand is a Lewis antigen. Particularly desirable are peptido-mimetics of the Lewis antigens SA-Le$^a$, SA-LeX, and LeY. The illustrative peptides described below may be modified, as described in more detail herein, to improve anti-adhesion properties and to increase their stability to degradation in vivo.

Desirable compositions of this invention contain one or more of the following peptido-mimetics which mimic the topography of the E-selectin ligand: ASAVNLYIPTQE [SEQ ID NO:84], VYLAPGRISRDY [SEQ ID NO:85], VYLAPGRFSRDY [SEQ ID NO:86], CTSHWGVLSQRR [SEQ ID NO:87], RVLSPESYLGPS [SEQ ID NO:88], RVLSPESYLGPA [SEQ ID NO:89], VGNGVLMGRRG [SEQ ID NO:90], RVLSPESYLGPA [SEQ ID NO:92], GNCRYIGLRQFG [SEQ ID NO:93], DIRVEPGGGYTH [SEQ ID NO:94], APIHTYTGRARG [SEQ ID NO:96], and RHTCVRSCGHDR [SEQ ID NO:97].

Similarly, exemplary peptido-mimetics of SA-Le$^a$ include, without limitation, VGIWSWSEGSR [SEQ ID NO: 102], RCSVGVPFTMES [SEQ ID NO:103], QDGVWEHVLEGG, [SEQ ID NO:104], DLWDWVGKPAG [SEQ ID NO:1], VELSGRGGLCTW [SEQ ID NO:105], VIGAASHDEDVD [SEQ ID NO:106], TIEPVLAEMMG [SEQ ID NO:107], DKETFELGLFDR [SEQ ID NO:108], FSGVRGVYESRT [SEQ ID NO:109], PDDAPMHSTRVE [SEQ ID NO:110], STGLMVDFLEPG [SEQ ID NO: 91], AKTFGLEHGCEA [SEQ ID NO: 95], GGTVEVWSIKGG [SEQ ID NO: 115], DHFSQAGSSNHH [SEQ ID NO: 116]; DDPVTPVIDFGK [SEQ ID NO: 117], and RDGLIDFVVAGT [SEQ ID NO: 118].

As described in the examples below, families of mimics of carcinoma-associated antigens that represent SA-Le$^a$, in particular, were identified from a combinatorial peptide library using MAb NS 19-9 specific for this carbohydrate structure. One of the peptides, DLWDWVVGKPAG [SEQ ID NO: 1], was selected that specifically competes for binding of MAb for SA-Le$^a$. This peptide displays an ability to partially inhibit neutrophil recruitment in an acute inflammation model in vivo. As described below, this peptide was analyzed by systematic amino acid replacements to identify optimal conformationally stabilized SA-Le$^a$ mimics with higher affinity using a solid phase peptide array library. Comparison of signal intensities revealed significant differences in MAb binding as a result of substitutions, in particular at the N-terminus. Substitution analysis allowed for delineation of key residues that were sensitive to replacement. MAb NS19-9 discriminated against multiple amino acid substitutions affecting its recognition. Specific residues within this peptide were identified that may contribute to the mimicry of carbohydrate structure by the peptide.

On the other hand MAb NS19-9 could tolerate replacement of the lead peptide sequence by a variety of amino acids. These substitutions did not abrogate binding, suggesting that they did not affect the structural specificity required for MAb recognition. Different amino acids in themselves can act as structural mimics within an identified peptide and bind through non-specific interactions. The different consensus sequences among the families of peptides identified with the same MAb from the random peptide library or sequences without an obvious consensus characterized in previous studies support the notion that indeed different amino acid residues provide structural similarity. Alternatively, different consensus sequences mimic different topographies of the carbohydrate epitope recognized by the antibody.

The identification of several cross-reactive peptides displaying higher NS19-9 binding further delineate specific residues that may improve upon peptide mimicry of the carbohydrate structure. Several substitutions within the C-terminus, in particular with amino acids containing carboxyl groups that increased MAb binding, were identified suggesting an important role of polar interactions in binding affinity. The strongest signal however resulted from the single amino acid substitution of Phe for the Trp at position 5, creating the SA-Le$^a$ peptidomimetic DLWDFVVGKPAG [SEQ ID NO: 63].

The present invention demonstrates that peptides mimicking SA-Le$^a$ are able to bind surfaces of proteins specific for these structures and thus they can act as antagonists for the recognition of the cognate carbohydrate antigen or ligand. In vivo oligosaccharide dependent reduction of metastasis formation may be a function of the interruption of these interactions. Antagonists interfere with the metastatic process at the level of cellular adhesion and blood vessel formation since E-selectin and SA-LeX are expressed on actively growing blood vessels. Alternatively, peptide mimics act on signal transduction events mediated by selectins and their ligands and the in vivo consequences of selectin-ligand antagonism to the complex signal transduction processes associated with selectin-dependent cell adhesion.

Certain exemplary peptidomimetics of LeY include the peptides TKRPDLIVDPIP [SEQ ID NO:98], DEVRPDLISTEE [SEQ ID NO: 99], NLRPKYIXLDAD [SEQ ID NO:100), and TLIAFADLVDVI [SEQ ID NO: 101].

Peptides mimicking carbohydrate antigens retain conformational properties of cognate carbohydrate structures and can block recognition of cells expressing such ligands in vivo. Thereby, they can mediate anti-metastatic functions as demonstrated by blocking of experimental metastasis. Thus, the peptides identified above which mimic the topography of the E-selectin ligand and/or the other Lewis antigens can be employed in pharmaceutical compositions. Such peptidomimetics are useful in pharmaceutical compositions directed toward the treatment of cancer, and the prevention and/or inhibition of metastases (see, e.g., Example 14). Such peptides may also be used in pharmaceutical treatments to block selectin-dependent interactions, e.g. diminishing the inflammatory response (see, e.g., Example 8).

The above peptido-mimetics and others which may be identified by use of the assays referred to below may be further modified to increase or enhance the stability of such peptides for in vivo use or to enhance the binding abilities of these peptido-mimetics. Peptido-mimetics according to this invention includes peptido-mimetics such as those identified specifically above, which are modified to increase their stability in vivo.

For example, the incorporation of unnatural amino acids (e.g., D configuration amino acids) at the N or C termini, the most frequent peptide degradation sites, may improve the pharmacological properties of the peptides, without loss of the binding efficacy. Another modification involves incorporating onto the N-terminus of the peptide a moiety which can provide a net positive charge on the N-terminus of the peptide. Such moieties can include straight chain, branched, cyclic or heterocyclic alkyl groups, straight chain, branched, cyclic or heterocyclic alkanoyl groups, a positively charged reporter group; and/or one or up to 15 additional amino acids independently selected from L-configuration or D-configuration amino acids, optionally substituted with a straight chain, branched, cyclic or heterocyclic alkyl group, a straight chain, branched, cyclic or heterocyclic alkanoyl group, or a reporter group. The amino acids may be naturally occurring amino acids or unnatural amino acids, such as D configuration amino acids, or amino acids which have been cyclized by the insertion of modifying sugars, imide groups and the like. One specific embodiment of an N-terminal moiety is the positively charged 1-aminocyclo-hexane carboxylic acid. Another is a single positively charged amino acid such as L-Val- or D-Val-. In still other embodiments, such additional amino acids are modified by an acetyl group, providing that a net positive charge results. In still other embodiments of modified peptides, the N-terminal group is a positively charged moiety which can function as a reporter group for detection purposes.

These peptides may also be modified to cyclize the peptide by joining the N- and C-termini of the peptide. Additional amino acids or spacers may be introduced into the peptides also form spacers, which may be needed to cyclize the peptide by bridging between the N- and C-termini of the peptide. Spacers are sequences of greater than 3 amino acids which are interposed between the normal N-terminus and C-terminus of the modified peptidomimetic. These spacers permit linkage therebetween without imposing any adverse restraint upon the molecular structure. Spacers may also contain restriction endonuclease cleavage sites to enable separation of the sequences, where desired. Desirably, spacers duplicate a portion of the peptide. Suitable spacers or linkers are known and may be readily designed and selected by one of skill in the art.

Similarly, the C terminus of a peptido-mimetic of this invention may be a free hydroxyl, an amide, an imide, a sugar, or a sequence of one or up to about 15 additional amino acids, optionally substituted with a free hydroxyl, an amide, an imide or a sugar. The C-termini may also be modified in the same manner as the modified N-ternmini, described above. As one specific embodiment, the C terminus of the a peptido-mimetic may be modified with 2-acetamido-2-deoxyglucose. Another specific embodiment is the addition to the C-terminal amino acid of the peptido-mimetic of triacetyl 2-acetamido-2-deoxyglucose. In another embodiment of a modified peptides of this invention, the C-terminal amino acid is modified by the addition of a β-acetyl-2,3-diamino propionic acid group.

Still another modification of the peptides of this invention includes the addition into the peptides of two adjacent amino acids which are resistant to cleavage by endopeptidases. Still another modification involves replacing conventional inter-residue amide bonds by bonds resistant to proteases, such as, a thioamide bond or a reduced amide bond. Such modifications of the bonds between amino acids may change the conformation of the peptide. A variety of methods for producing non-natural amino acids are known and insert modified inter-residue bonds, and/or cyclize the peptides may be selected by one of skill in the art. Other backbone-modifications of these peptides are also anticipated to improve proteolytic stability and yield analogs with slightly modified activity spectrum. The specific peptide described above may also be readily modified by replacing one or more amino acids with another, by substituting individual amino acids with chemical components or labels or by other peptide modification methods known to those of skill in the art. Such modifications may be made to enhance stability of the peptide in a pharmaceutical composition or to enhance the binding ability of the peptido-mimetic to the desired ligand [See, e.g., Example 13]. Such modifications include peptide modifications disclosed in J. E. Oh et al, *J. Peptide Res.*, 54:129–136 (1999), incorporated herein by reference.

Peptide multivalency is another modification that should result in higher affinity binding as compared to low affinity interaction with monovalent peptides. Multivalency should increase peptide/EC interaction and lower concentration of multiple antigen peptides needed to block it. The generation of high affinity ligands might require formation of a "clustered oligosaccharide patch" or a "clustered anionic patch" or a combination of polypeptide backbone and modifications such as sulfation Thus, these peptides may be employed individually, or presented in a multivalent form, such as a multiple antigenic peptide ("MAP", also referred to as an octameric lysine core peptide) construct. Such a construct may be designed employing the MAP system described by Tam, *Proc. Natl. Acad. Sci. USA*, 85:5409–5413 (1988), D. Posnett et al., *J. Biol. Chem.*, 263(4):1719–1725 (1988), J. Tam, *Vaccine Research and Developments*, Vol. 1, ed. W. Koff and H. Six, pp. 51–87 (Marcel Deblau, Inc., New York 1992)]. In any multivalent form, each peptide may be optionally separated by amino acid spacers, which are defined above.

One may generate homologous amino acid or polynucleotide sequences which share significant homology with the above-identified peptido-mimetics or with other peptido-mimetics identified by the methods of this invention. Sequence homology for polypeptides, which is also referred to as sequence identity, is typically measured using sequence analysis software. See, e.g., the Sequence Analysis Software Package of the Genetics Computer Group (GCG), University of Wisconsin Biotechnology Center, 910 University Avenue, Madison, Wis. 53705. Protein analysis software matches similar sequences using a measure of homology assigned to various substitutions, deletions and other modifications, including conservative amino acid substitutions. For instance, GCG contains programs such as "Gap" and "Bestfit" which can be used with default parameters to determine sequence homology or sequence identity between closely related polypeptides, such as homologous polypeptides from different species of organisms or between a wild type protein and a mutein thereof. A preferred algorithm when comparing a specific polypeptide sequence to a database containing a large number of sequences from different organisms is the computer program BLAST, especially blastp or tblastn (Altschul et al., 1997, herein incorporated by reference). Database searching using amino acid sequences can be measured by algorithms other than blastp known in the art, e.g., Fasta, a program in GCG Version 6.1. The term "substantial homology" or "substantial similarity," when referring to a nucleic acid or fragment thereof, indicates that, when optimally aligned with appropriate nucleotide insertions or deletions with another nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases, as measured by any well-known algorithm of sequence identity, such as Fasta, as discussed above.

B. Methods of Preparing Peptides of this Invention

The peptides of the invention may be prepared conventionally by resort to known chemical synthesis techniques, e.g., solid-phase chemical synthesis, such as described by Merrifield, *J. Amer. Chem. Soc.*, 85:2149–2154 (1963), and J. Stuart and J. Young, *Solid Phase Peptide Synthelia*, Pierce Chemical Company, Rockford, Ill. (1984), or detailed in the examples below. Chemical synthesis methods are particularly desirable for large-scale production of such peptides. A variety of methods for producing the above-identified modifications of the peptides, e.g., non-natural amino acids, are known and may be selected by one of skill in the art.

Alternatively, the peptides of this invention may be prepared by known recombinant DNA techniques by cloning and expressing within a host microorganism or cell a DNA fragment carrying a nucleic acid sequence encoding one of the above-described peptides [See, e.g., Sambrook et al., *Molecular Cloning. A Laboratory Manual.*, 2d Edit., Cold Spring Harbor Laboratory, New York (1989)]. Conventional molecular biology techniques, and site-directed mutagenesis may be employed to provide desired modified peptide sequences.

The preparation or synthesis of the peptido-mimetics disclosed herein is well within the ability of the person having ordinary skill in the art using available material. The synthetic methods are not a limitation of this invention.

C. Pharmaceutical Preparations of this Invention

The selected peptido-mimetics are desirably formulated into pharmaceutical compositions suitable for administering to a mammalian subject, preferably a human. Such formulations comprise one or more of the peptides identified above, combined with a pharmaceutically or physiologically acceptable carrier, such as sterile water or sterile isotonic saline. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Such formulations may further comprise one or more additional ingredients including, but not limited to, suspending, stabilizing, or dispersing agents. In one embodiment of a formulation for parenteral administration, the peptide is provided in dry (i.e., powder or granular) form for reconstitution with a suitable vehicle (e.g., sterile pyrogen-free water) prior to parenteral administration of the reconstituted composition.

Other parenterally-administrable formulations which are useful include those which comprise the peptide in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt. The peptides of the present invention may be administered by oral, intraperitoneal, intramuscular and other conventional routes of pharmaceutical administration.

Pharmaceutical compositions of the present invention may be administered either as individual therapeutic/prophylactic agents or in combination with other agents. They can be administered alone, but are generally administered with a pharmaceutical carrier selected on the basis of the chosen route of administration and standard pharmaceutical practice. One of skill in the pharmaceutical arts may readily design acceptable pharmaceutical formations for delivery of the peptido-mimetics of this invention with recourse to well-known information on pharmacology and with use of commercially available materials, in view of the teachings herein.

The "effective amount" of the peptide of the invention present in each effective dose is selected with regard to consideration of the condition being treated, the patient's age, weight, sex, general physical condition and the like. The amount of active component required to induce a desired effect without significant adverse side effects varies depending upon the pharmaceutical composition employed and the optional presence of other components. Generally, for the compositions containing peptide, fusion protein, or MAP, each daily dose will comprise between about 50 $\mu$g to about 2 mg of the peptide per mL of a sterile solution per kg body weight. Another desired daily dosage of active ingredient can be about 0.0001 to 1 grams per kilogram of body weight. Another desired dosage range can be about 0.1 to 100 milligrams per kilogram of body weight. Still another dosage is in the range of 0.5 to 50 milligrams per kilogram of body weight, and preferably 1 to 10 milligrams per kilogram per day. Other dosage ranges may also be contemplated by one of skill in the art.

Initial doses may be optionally followed by repeated administration for a duration selected by the attending physician. Dosage frequency may also depend upon the factors identified above, and may range from daily dosages to once or twice a week i.v. or i.m., for a duration of about 6 weeks. The compositions of the present invention can also be employed in treatments for chronic inflammatory ailments or for long term treatment of cancer patients for a period to be selected by the physician.

D. Methods of the Invention

The peptides described above and the pharmaceutical compositions containing them may be employed in therapeutic methods or in in vitro methods for the development of other pharmaceutical agents. Each of the methods described employs the peptido-mimetic to interfere with, or inhibit, the binding of a desired carbohydrate antigen with its normal receptor or adhesion molecule, so as to prevent or inhibit an undesired therapeutic result. It is anticipated that the therapeutic methods may be performed ex vivo or in vivo.

Thus, one embodiment of the present invention provides a method of modulating binding of an adhesion molecule to a carbohydrate ligand. According to this method, an adhesion molecule, such as a selectin, is contacted with a peptido-mimetic which mimics the topography of the carbohydrate ligand. Binding of the adhesion molecule by the peptido-mimetic in place of the normal ligand thus modulates, or reduces the amount of binding between the adhesion molecule and its carbohydrate ligand and thereby suppresses or reduces the normal effect of such binding. Modulating binding of an adhesion molecule, (e.g., E-selectin) to a carbohydrate ligand refers to any reduction or increase in binding of the selectin to the carbohydrate ligand wherein the difference in binding results in a desired therapeutic effect. It is desirable for this method that the carbohydrate ligands and adhesion molecules are present on the surface of the cells in such a manner as to allow binding of the adhesion molecule to the ligand and/or to the peptido-mimetic of the ligand.

The peptido-mimetics of this invention may be used in treatments for cancer. For example, one embodiment is a method of modulating adhesion of a tumor cell to an adhesion molecule on an endothelial cell, e.g., a selectin. As above, the method comprises contacting the tumor cell with an effective amount of a peptido-mimetic (or a pharmaceutical composition containing the effective amount) of a carbohydrate ligand. By interfering with the binding between the tumor cell and its naturally occurring selected binding partner, this method provides a way of inhibiting or otherwise modulating the biological activity mediated by the natural adhesion of the tumor cell to the endothelial cell. This method provides a therapy for cancer patients. The peptido-mimetics described herein may be used in this method.

In another method of treating cancer in a mammal, an effective amount of a peptido-mimetic of a carbohydrate ligand is administered to the mammal. Such treatment also reduces the adhesion of tumor cells to endothelial cells in the mammal, thereby reducing metastasis of the cancer. An "adherence modulating dose" refers to any amount of a peptido-mimetic, or any combination of peptido-mimetics, of a carbohydrate ligand which affects the adherence of a cell bearing the carbohydrate ligand to an adhesion molecule on endothelial cells. By "adherence reducing dose" is any amount of a peptido-mimetic of a carbohydrate ligand which, when administered to a mammal, reduces the binding of an adhesion molecule to a carbohydrate ligand. This dose reduces the adhesion of certain cells which present carbohydrate ligands on their surfaces (e.g., tumor cells and neutrophils) to endothelial cells, compared with the adhesion of those same cells to endothelial cells in the mammal prior to the administration of the peptido-mimetic.

Preferred embodiments of this method are illustrated in the examples below which demonstrate the use of a peptidomimic of a carbohydrate tumor associated antigen to reduce the number of experimental metastasis in vivo. SA-Le$^a$ provides the critical carbohydrate ligand for the adhesion molecule, E-selectin, that facilitates the initial steps involved in a cascade of tumor cell-endothelial interactions leading to metastatic spread. The use of the peptides of this invention which mimic the E-selectin ligand, SA-Le$^a$, inhibit metastasis of tumor cells expressing this structure. The abrogated tumor growth in E-selectin knock-out (KO) mice are demonstrated in the examples below, which provide evidence that SA-Le$^a$ and E-selectin are important in metastasis formation.

Briefly described, B16F10FTIII melanoma cells employed in a metastasis model express SA-Le$^a$ carbohydrate antigen and form lung tumors after i.v. inoculation through the tail vein. Tumor colonization appears to be highly E-selectin dependent, as the incidence of metastasis was completely abrogated in E-selectin KO mice. The initial stages required for tumor colonization are dependent not only on adhesion molecules inducible on endothelial cells, but also on the ligands expressed on tumor cells. The expression of E-selectin ligand, SA-Le$^a$, is likely to contribute to the metastasis of cells expressing this structure. The 50% inhibition of tumor metastasis achieved upon administration of the peptide antagonist of SA-Le$^a$ expressed on the B16F10 tumor cell surface can be explained by interruption of the initial steps of cascade of inhibitory events initiated by tumor cell adhesion with this conformational equivalent of the SA-Le$^a$ structure. These findings suggest that expression of SA-Le$^a$ leads to tumor specific colonization in vivo.

Gross histological examination of the lungs (not shown) did not reveal significant differences in the appearance of the small spherical tumor nodules between animals treated with peptide and the control group. This observation suggests that the peptide treatment may indeed block the initial stages of adhesion to lung endothelium required for initiation of tumor cell migration into the subendothelial space, resulting in reduced number of nodules but not tumor growth after the micrometastases are established. Although the reduced number of metastases was the prevalent effect of peptide treatment as compared with the control group, large lung tumor masses were observed in untreated animals.

The examples below provide evidence that members of all cell adhesion molecule families and carbohydrate structures, SA-Le$^a$ and SA-LeX, expression are associated with capillary tube formation and neovascularization necessary to maintain metastasis. This indicates that the anti-angiogenic mechanism of tumor growth inhibition in peptide treated animals also takes place. Similarly, the complete inability of tumor cell colonization in the lungs of E-selectin KO animals may result from the lack of initial adhesion steps mediated by this adhesion molecule, as well as impaired angiogenesis, in which E-selectin is involved. E-selectin is one of the few adhesion molecules truly restricted to activated endothelium, thus E-selectin may be used to selectively target activated and/or proliferating endothelium in vivo not only by blocking adhesion of tumor cells to EC, but also by halting the neovascularization processes. Consequently, proliferating microvascular endothelium presents an unique and universal target for anti-cancer therapy.

In still another therapeutic embodiment of this invention, a method for inhibiting an inflammatory response in a mammal is provided. This method involves contacting an endothelial cell with an effective amount of a peptido-mimetic of a carbohydrate ligand, thereby modulating adherence of neutrophils to endothelial cells. By "modulating neutrophil adherence," as the term is used herein, is meant any difference in the adherence of a neutrophil to an endothelial cell in the presence of a peptido-mimetic of a carbohydrate ligand compared with the adherence of a neutrophil to an endothelial cell in the absence of the peptido-mimetic of a carbohydrate ligand. By "inhibiting an inflammatory response," as the term is used herein, is meant decreasing the inflammatory response in a mammal. Inflammatory response refers to the physiological response in an animal which includes, but is not limited to, recruitment of neutrophils to the site of inflammation and/or the adherence of neutrophils to endothelial cells. In an exemplary embodiment, one inflammatory response which may be treated by the present invention is peritonitis (i.e., an irritation of the peritoneum). A substantial reduction in pathology of inflammation is achieved upon 30% reduction of neutrophil recruitment in the inflammatory model illustrated below. However, this aspect of the invention is not limited to the manner in which inflammation is caused or the tissue in which inflammation is present and/or treated. The peptido-mimetics described herein are particularly useful in this aspect of the invention.

Still other conditions mediated by interaction between adhesion molecules and their carbohydrate ligands may be treated by the use of peptidomimetics of either the antigen or the ligand in a manner similar to that disclosed above.

E. Cells of the Invention

In a further aspect, the invention provides a cell (e.g., yeast, bacteria, phage, or mammalian) which is constructed to display an exogenous peptido-mimetic of a Lewis antigen or a selectin on the surface of the cell. More particularly, this invention is directed to cells displaying the specific peptides disclosed herein, either alone or as fusion proteins, on the cell surface. One manner in which this may be obtained is described in Example 1, through the use of a random peptide library. Analogous cells, other than *E. coli* may be produced by similar methods. See the cells described in Examples 10 and 14, which also provide instruction on the provision of cells developed to express peptido-mimetics.

E. Use of Peptides and Methods for Identification of Other Useful Pharmaceutical Peptides or Compounds Use of additional combinatorial synthetic chemistry technologies will allow for improved antagonists of tumor cell adhesion, leading to the further development of agents with greatly enhanced therapeutic potential. Using a combinatorial approach based on functional equivalence of chemically dissimilar molecules sharing common surface topology instead of derivatized parental structures is effective in developing antagonists of physiologically important molecular interactions.

As one embodiment, the invention provides a method for identifying an additional peptido-mimetic of a carbohydrate ligand which affects the binding of the carbohydrate ligand to a binding partner. The method comprises the steps of: (a) contacting the binding partner with a peptido-mimetic and (b) comparing the binding of the binding partner of (a) to the carbohydrate ligand with the binding of the same binding partner which is not contacted with the peptido-mimetic to the carbohydrate ligand. The level of binding of the binding partner contacted with the peptido-mimetic to the carbohydrate ligand is compared with the level of binding of the binding partner not contacted with the peptido-mimetic with the same carbohydrate ligand. Any significant change in these two levels of binding is an indication that the peptido-mimetic affects the binding of the carbohydrate ligand to the binding partner. In one embodiment the binding partner is an adhesion molecule located on an endothelial cell.

In another embodiment, the carbohydrate ligand is located on the surface of a tumor cell and the adhesion molecule is a selectin, e.g., E-selectin. Any change in the level of binding of E-selectin or any other adhesion molecule contacted with the peptido-mimetic to the carbohydrate ligand compared with the level of binding of E-selectin or any other adhesion molecule not contacted with the peptido-mimetic with the same carbohydrate ligand is an indication that the peptido-mimetic affects the binding of the tumor cell to the adhesion molecule.

Another method of identifying a peptido-mimetic of a carbohydrate ligand which affects angiogenesis is provided by this invention. The method involves contacting a primary capillary endothelial cell with a peptido-mimetic of a carbohydrate ligand, e.g., a Lewis antigen. Any difference between capillary tube formation observed by the cell contacted with the peptido-mimetic is compared to the capillary tube formation of the cell which is not contacted with the peptido-mimetic. Any significant change in capillary tube formation is an indication that the peptido-mimetic affects angiogenesis. A number of assays exist in the art for the determination of effects on angiogenesis, including microscope examination of capillary tube formation in tissue [See, e.g., Nguyen et al, cited above]. It should be understood that this same method may be employed using other means of determining changes in angiogenesis caused by a similar use of peptido-mimetics.

Yet another method of identifying a peptido-mimetic which affects adhesion of a selected cell to an endothelial cell involves contacting an endothelial cell with a peptido-mimetic of a carbohydrate ligand located on the endothelial cell. The binding of the endothelial cell contacted with the peptido-mimetic to the ligand is compared to the binding of an endothelial cell which has not been contacted with the peptido-mimetic to the ligand. Any change in the levels of binding is an indication that the peptido-mimetic affects binding of the selected cell to the endothelial cell. In one embodiment, the selected cell is a tumor cell. In another embodiment, the selected cell is a neutrophil. In still another embodiment, the carbohydrate ligand is located on the surface of a tumor cell and the adhesion molecule of the ligand is located on a human umbilical cord vein endothelial cell (HUVEC). Any change in binding caused by the peptido-mimetic is an indication that the peptido-mimetic affects the binding of the tumor cell to HUVEC. This method is also not limited to the identity of the selected cells, nor to the assays used to detect differences in binding.

The invention further provides a method of identifying a peptido-mimetic of a carbohydrate ligand which is involved in inflammatory processes. That method involves administering an inflammation-inducing substance (e.g., a peritonitis-inducing substance) into a suitable tissue or organ of a mammal. Thereafter, an effective amount of a peptido-mimetic of the carbohydrate ligand is administered at the site or area of the inflammation. A control mammal having a similar inflammation at the same site is not treated. Any effect on inflammation which is observed in the treated mammal vs. the control, such as neutrophil influx into the site of inflammation, is an indication that the peptido-mimetic affects inflammation. In one embodiment, the inflammation inducing substance causes peritonitis and the site of inflammation is the peritoneam. The levels of neutrophil influx in the peritoneum of the treated mammal are observed to be lower that the levels of neutrophil influx in the peritoneum of the control. This result is an indication that the peptido-mimetic inhibits an inflammatory response. This method is not limited by the method of inducing inflammation or the site of inflammation or the indication of inflammation that is assessed. For example, myeloperoxidase activity could be assayed in place of neutrophil recruitment. The site and method of administration of the peptido-mimetic and the assayed indication may be selected by one of skill in the art.

In general, the present invention provides a method of producing peptido-mimetics of Lewis antigens, particularly those not including APWLYAGP [SEQ ID NO: 83]. This method comprises the step of: (a) screening a random peptide library, the peptides expressed as fusion proteins on the surface of bacterial clones, with antibodies specific for the Lewis antigens and/or with adhesion molecule constructs, e.g., molecules expressed as fusion proteins. One such example is the E-selectin immunoglobulin fusion protein used in Example 2. Other such fusion molecules may be used similarly in this step, and (b) The clones which bind the antibodies or adhesion molecule constructs. The clones which bind the antibodies or adhesion molecule constructs produce peptido-mimetics of the Lewis antigens. This method is exemplified by Examples 1 and 2 below. Modifications of these methods are contemplated in the performance of this method. Such modifications are readily made by one of skill in the art.

The peptides and polynucleotide sequences of the present invention may also be used in the screening and development of chemical compounds, small molecules or proteins which mimic the structure or activity of the carbohydrate ligands, and thus have utility as therapeutic drugs for the treatment of cancer and inflammation. Competition assays, such as the ELISA described in Example 3, may be employed and readily designed for such use. Additionally, a compound which has structural similarity to the peptido-mimetic, or the binding of the peptide to the ligand may also be computationally evaluated and designed by means of a series of steps in which chemical entities or fragments are screened and selected for their ability to associate with the peptides of this invention.

Specialized computer programs that may also assist in the process of selecting fragments or chemical entities similar to the peptides, or entities which can interact with the peptides and thus mimic the receptor, include the GRID program available from Oxford University, Oxford, UK. [P. J. Goodford, "A Computational Procedure for Determining Energetically Favorable Binding Sites on Biologically Important Macromolecules", J. Med. Chem., 28:49–857 (1985)]; the MCSS program available from Molecular Simulations, Burlington, Mass. [A. Miranker and M. Karplus, "Functionality Maps of Binding Sites: A Multiple Copy Simultaneous Search Method", Proteins: Structure, Function and Genetics, 11:29–34 (1991)]; the AUTODOCK program available from Scripps Research Institute, La Jolla, Calif. [D. S. Goodsell and A. J. Olsen, "Automated Docking of Substrates to Proteins by Simulated Annealing", Proteins: Structure, Function, and Genetics, 8:195–202 (1990)]; and the DOCK program available from University of California, San Francisco, Calif. [I. D. Kuntz et al, "A Geometric Approach to Macromolecule-Ligand Interactions", J. Mol. Biol., 161:269–288 (1982)], software such as Quanta and Sybyl, followed by energy minimization and molecular dynamics with standard molecular mechanics force fields, such as CHARMM and AMBER. Additional commercially available computer databases for small molecular compounds include Cambridge Structural Database, Fine Chemical Database, and CONCORD database [for a review see Rusinko, A., Chem. Des. Auto. News, 8:44–47 (1993)].

Once suitable chemical entities or fragments have been selected, they can be assembled into a single compound. Assembly may proceed by visual inspection of the relationship of the fragments to each other on the three-dimensional image displayed on a computer screen in relation to the structure of the peptido-mimetic of this invention. Useful programs to aid one of skill in the art in connecting the individual chemical entities or fragments include the CAVEAT program [P. A. Bartlett et al, "CAVEAT: A Program to Facilitate the Structure-Derived Design of Biologically Active Molecules", in Molecular Recognition in Chemical and Biological Problems", Special Pub., Royal Chem. Soc. 78, pp. 182–196 (1989)], which is available from the University of California, Berkeley, Calif.; 3D Database systems such as MACCS-3D database (MDL Information Systems, San Leandro, Calif.) [see, e.g., Y. C. Martin, "3D Database Searching in Drug Design", J. Med. Chem., 35:2145–2154 (1992)]; and the HOOK program, available from Molecular Simulations, Burlington, Mass.

Compounds that mimic a peptide of this invention or a ligand of the peptides may be designed as a whole or "de novo" using either an empty active site or optionally including some portion(s) of a known ligand(s). Suitable methods describing such methods include the LUDI program [H.-J. Bohm, "The Computer Program LUDI: A New Method for the De Novo Design of Enzyme Inhibitors", J. Comp. Aid. Molec. Design, 6:61–78 (1992)], available from Biosym Technologies, San Diego, Calif.; the LEGEND program [Y. Nishibata and A. Itai, Tetrahedron, 47:8985 (1991)], available from Molecular Simulations, Burlington, Mass.; and the LeapFrog program, available from Tripos Associates, St. Louis, Mo. Other molecular modelling techniques may also be employed in accordance with this invention. See, e.g., N. C. Cohen et al, "Molecular Modeling Software and Methods for Medicinal Chemistry", J. Med. Chem., 3:883–894 (1990). See also, M. A. Navia and M. A. Murcko, "The Use of Structural Information in Drug Design", Current Opinions in Structural Biology, 2:202–210 (1992). For example, where the structures of test compounds are known, a model of the test compound may be superimposed over the model of the peptide of the invention. Numerous methods and techniques are known in the art for performing this step, any of which may be used. See, e.g., P. S. Farmer, Drug Design, Ariens, E. J., ed., Vol. 10, pp 119–143 (Academic Press, New York, 1980); U.S. Pat. No. 5,331,573; U.S. Pat. No. 5,500,807, C. Verlinde, Structure, 2:577–587 (1994); and I. D. Kuntz, Science, 25:1078–1082 (1992). The model building techniques and computer evaluation systems described herein are not a limitation on the present invention.

Thus, using these computer evaluation systems, a large number of compounds may be quickly and easily examined and expensive and lengthy biochemical testing avoided. Moreover, the need for actual syntheses of many compounds is effectively eliminated. Once identified by the modelling techniques, the proposed "new antibacterial" compound may be tested for bioactivity using standard techniques, such as the assays of the examples below.

The invention is further described in detail by reference to the following, experimental examples. These examples are provided for purposes of illustration only, and are not intended to be limiting unless otherwise specified. Thus, the invention should in no way be construed as being limited to the following examples, but rather should be construed to encompass any and all variations which become evident as a result of the teaching provided herein.

EXAMPLE 1

Screening of a Random Peptide Library

To develop novel molecules to inhibit the adhesion of human adenocarcinoma cells to EC and, ultimately, to inhibit metastasis in vivo, peptides were derived from a 12-mer random peptide library. A diverse library of random dodecapeptides, displayed as flagellin-thioredoxin fusion proteins (FLITRX) on the surfaces of E. Coli bacterial cells, was obtained from Invitrogen (Carlsbad, Calif.) [LaVallie et. al., 1993, Bio/Technology, 11:187–193]. This library enables efficient isolation of bacteria displaying peptides with affinity to immobilized antibodies or to other binding proteins. The use of this library offered advantages over phage display in which the level of expression of phage coat protein genes is low and the selected peptides are usually unconstrained molecules with many degrees of conformational freedom. Moreover, no phage infection or isolation steps are necessary using, the FLITRX fusion protein system. Such highly diverse peptide libraries offer many distinct advantages over difficult chemical or enzymatic synthesis of complex carbohydrates, providing for the inexpensive and rapid identification and optimization of novel ligands.

Specifically, an aliquot of the FLITRX library containing at least $2\times10^{10}$ cells to ensure full representation of peptides, was grown to saturation for 15 hours in IMC/amp 100 medium (M9 medium containing 1 mM $MgCl_2$ supplemented with 0.5% glucose, 0.2% casamino acids and 100 µg/ml ampicillin). The expression of thioredoxin with incorporated 12-mer peptide sequence was induced by further 6 hours of incubation of a culture of $10^{10}$ cells, diluted 1:25 with fresh IMC/amp 100 medium containing 100 µg/ml tryptophan. The induced bacteria were panned on a MAb-coated tissue culture (20 µg/ml) plate followed by blocking with 1% nonfat milk containing 150 mM NaCl and 1%

α-methyl mannoside for 1 hour. The bound cells were washed gently. Eluted cells were collected by rinsing the plate with 10 ml of fresh IMC/amp 100 medium and then incubated at 25° C. until reaching saturation. The entire selection process was repeated four more times. Colonies of isolated bacteria were grown on ampicillin-containing plates. Individual colonies were isolated and grown as a small scale culture (2 ml) in IMC/amp 100 medium with tryptophan for 6 hours.

EXAMPLE 2

Protein Expression, Isolation and Sequencing

In the final selection cycle described above, the clones were tested for protein expression using sodium dodecyl sulfate-polyacrylamide gel electrophoresis (SDS-PAGE) followed by Western blotting [Towbin et al., 1979, *Proc. Natl. Acad. Sci. USA* 76:4350–4354] as follows. Specifically, each bacterial pellet was collected and dissolved directly in SDS-PAGE sample buffer containing SDS and β-mercaptoethanol. Proteins were separated using 12% polyacrylamide gel and transferred into nitrocellulose filters according to standard procedures. Expression of the FLITRX fusion protein-containing peptide sequences mimicking carbohydrate structures expressed by the bacterial clones was detected using one of the following monoclonal antibodies (10 pg/ml):

(1) MAb BR15-6A, which is specific for the carbohydrate ligand LeY [Rodeck et al., 1987, *Hybridoma* 6:389–401], (2) MAb NS19-9, which is specific for the carbohydrate ligand SA-Le$^a$ [Magnani et al., 1981, *Science* 212:55–56; Bechtel et al, 1990, *J. Biol. Chem.*, 265:2028–2037], and (3) MAb FH6, which is specific for the carbohydrate ligand SA-LeX [Fukushi et al., 1985, *Cancer Res.* 45:3711–3717].

E-selectin-immunoglobulin chimeric protein IgG (E-selectin-IgG; Centocor, Inc., Malvern, Pa.) [Geng et al., 1992, *J. Biol. Chem.* 267:19846–19853] was also used.

The expression and the location of thioredoxin on the nitrocellulose filter was confirmed after incubation of parallel filters with trxA-specific MAb (anti-Thio™) (Invitrogen, Carlsbad, Calif.). Following antibody binding, the filters were washed, incubated with horseradish peroxidase (HRP)-conjugated goat anti-mouse antibody, and then washed again. Finally, the filters were exposed to a freshly prepared mixture of a solution comprising luminol and oxidizing solution (1:1) for 1 minute, air-dried, and exposed on Reflection™ (NEN™ Life Sciences Products, Boston, Mass.). Only clones which displayed a strong signal on the Western blot with the respective MAb were selected for sequence identification. See Tables 1–3, discussed in detail in the Examples below.

The DNA of each clone was sequenced as follows. DNA was isolated from the selected bacteria using standard isopropanol precipitation in the presence of potassium acetate using a mini-column DNA purification column (Qiagen, Chatsworth, Calif.). The nucleotide sequences of the DNA from the selected bacteria were determined by the dideoxynucleotide chain termination method using specific primers using standard methods [see, e.g., Sambrook et al. 1989, *Molecular Cloning: A Laboratory Manual*, Cold Spring Harbor Laboratory, New York; Ausubel et al. 1997, *Current Protocols in Molecular Biology*, Green & Wiley, New York]. The peptides encoded by the sequenced DNA were either purchased commercially (Research Genetics, Inc., Huntsville, Ala.) and/or were chemically synthesized using FMOC-based, solid phase chemistry and were purified to homogeneity on a C-18 reverse-phase HPLC column. The structures were confirmed by fast-atom bombardment mass spectrometry.

For each sequenced dodecapeptide, a highly conserved core region was observed to be typically 3 to 5 amino acids long and the positional preference of these "consensus" residues within the dodecapeptide varied. Without wishing to be bound by theory, such positional preference may be a reflection of structural constraints of the inserted peptide imposed by thioredoxin which may limit the position for the antibody binding. Further examination of the sequences revealed that the peptides isolated by the BR15-6A and NS 19-9 MAbs and E-selectin-IgG fell into distinct consensus-sequence groups that discriminated between the MAbs and the lectin. The native carbohydrate antigens LeY and SA-Le$^a$ and the peptides bound only to the specific MAb or lectin used for their isolation. See, e.g., Tables 1–3 below.

Selected peptides were subject to assays for demonstrating whether the isolated peptides retain conformational properties of carbohydrates. Such assays include 1) direct binding to respective MAbs and E-selectin-IgG in solid phase; 2) inhibition of MAbs and E-selectin-IgG binding to the cognate carbohydrate ligands in solid phase; and 3) kinetic characterization of peptide binding to E-selectin using BIACORE methodology.

EXAMPLE 3

Competition Enzyme-Linked Immunosorbent Assay

The peptide competition/inhibition assays referred to throughout the following examples are performed as follows: Test peptides at concentrations ranging from 10 nM to 1 mM were preincubated with 100 µl of the MAb NS19-9 (5 µg/ml) diluted in 10% µ-globulin free horse serum/PBS at room temperature. Fifty µl of preincubated inhibition complex antibody-peptide is added to each well of 96-well plate and incubated at 30–37° C. for 1 hour. After 1 hour of incubation, MAb/peptide complex mixtures were transferred to wells precoated with a constant amount of neoglycoprotein containing coupled multivalent carbohydrate determinant (SA-Le$^a$-polyacrylamide matrix (SA-LeX-PAA or LeY-PAA) (5 µg/well) and allowed to bind for 1 hour followed by blocking with 10% γ-globulin-free horse serum for 2 hours at room temperature. Wells were washed with 100 µl PBS four times. Goat anti-mouse immunoglobulin G conjugated to horse radish peroxidase (Boehringer-Manheim, Indianapolis, Ind.) was diluted 1000-fold with 10% γ-globulin free horse serum/PBS and 100 µl was added in each well and incubated at 30–37° C. for 1 hour and washed with 100 µl PBS five times. Ten mg substrate for horse radish peroxidase, tetramethylbenzidine dichloride (TMB) (Sigma Chemical Co., St. Louis, Mo.) was dissolved in 10 ml of 0.05 M phosphate-citrate buffer, pH 5.0, containing 0.03% sodium perborate (Sigma Chemical Co.). One-hundred µl substrate was added in each well and incubated at room temperature for 10 minutes. The developed blue color was read at 450 nm after stopping the reaction with 100 µl 1M phosphoric acid. Fifty % inhibitory concentration ($IC_{50}$) was calculated by non-linear least-squares regression to a four-parameter logistic equation. The results of various competition assays performed as described are detailed in the following examples.

EXAMPLE 4

Peptido-Mimetics of Lewis Y and SA-Le$^a$

A. Le-Y

Peptides were isolated using MAb BR15-6A as described in Example 2 above. BR15-6A inhibits adhesion of human tumor cells to EC in E-selectin-independent mode. The family of peptides isolated using BR15-6A (Table 1), which mimics the LeY carbohydrate, also demonstrates the consensus sequence motif RPDL [SEQ ID NO:113]. This motif was also recognized by another LeY-specific MAb, BR55-2, suggesting that the basis for this cross-reactivity is structural mimicry.

The isolated sequences of the families of peptides mimicking LeY can be compared with a putative peptide APWLYAGP [SEQ ID NO:83] identified previously by phage display panning with another anti-LeY antibody [Hoess et al., 1993, *Gene* 128:43–49]. This result indicates that the same consensus sequences contribute to the mimicry of the carbohydrate structure and are responsible for the topological similarity with the carbohydrate antigen.

On the other hand, comparison of these three MAbs demonstrated their different binding specificity for LeY carbohydrate structure, suggesting that they recognize different epitopes displayed by the hexasaccharide [Blaszczyk-Thurin et al., 1987, *J. Biol. Chem.* 262:372–379; Rodeck et al., 1987, *Hybridoma* 6:389–401; Pastan et al., 1991, *Cancer Res.* 51:3781–3787]. Thus, the peptide topological equivalents of the LeY carbohydrate very likely represent overlapping epitopes common for all LeY-specific MAbs tested. Examples of peptide sequence families mimicking LeY structure are listed in Table 1 below.

TABLE 1

| Peptide Sequence | SEQ ID NO |
| --- | --- |
| TKRPDLIVDPIP | 98 |
| DEVRPDLISTEE | 99 |
| NLRPKYIXLDAD | 100 |
| TLIAFADLVDVI | 101 |
| GLDLLGDVRIPVVRR | 119 |
| VGITGFVDPLPLRLL | 120 |

Peptide SEQ ID NO: 99 from the family of LeY-mimicking peptides was selected because it contained a consensus motif which appeared in multiple bacterial isolates after five rounds of panning with the BR15-6A MAb. This peptide was chemically synthesized and its binding to BR15-6A MAb was evaluated. Dose-dependent binding of the MAb to solid phase coated peptide at concentrations of 1 nM to 1 mM was demonstrated using enzyme-linked immunosorbent assay (ELISA). This indicates that the peptide was recognized by the MAb and that the identified sequence DEVRPDLISTEE [SEQ ID NO: 99] represents a putative epitope for the MAb. This peptide was demonstrated to inhibit MAb BR15-6A binding to the carbohydrate structure of LeY. It likely represents a conformational mimic of the LeY structure. This peptide is further evaluated in competition assays with native LeY containing neoglycoprotein and LeY-specific MAbs BR15-6A and BR55-2.

B. SA-Le$^a$

Two distinct consensus sequences GXWXXVLEG [SEQ ID NO:111] and VVGXP [SEQ ID NO:112] were identified in families of peptides isolated with MAb NS 19-9, which recognizes E-selectin ligand, SA-Le$^a$. The structural relevance of isolation of these two motifs by a single MAb is unclear. Without wishing to be bound by theory, these motifs indicate the following: peptides based on two different motifs isolated with the same MAb can mimic different structural topographies of the cognate SA-Le$^a$ carbohydrate. These subsets of peptides likely represent non-overlapping surfaces of cognate antigen, and peptide binding to MAb occurs at separate sites. Peptide SEQ ID NO:1 from NS19-9 family II mimicking SA-Le$^a$ ligand was selected based on the presence of consensus motif which appeared in multiple bacterial isolates after five rounds of panning. Table 2 identifies peptide sequence families I and II mimicking SA-Le$^a$ carbohydrate structure. Table 3 identifies peptide sequence family III mimicking SA-Le$^a$ carbohydrate structure.

TABLE 2

| FAMILY I | | FAMILY II | |
| --- | --- | --- | --- |
| Peptide Sequence | SEQ ID # | Peptide | SEQ ID # |
| VGIWSVVSEGSR | 102 | RCSVGVPFTMES | 103 |
| QDGVWEHVLEGG | 104 | DLWDWVVGKPAG | 1 |
| VELSGRGGLCTW | 105 | VIGAASHDEDVD | 106 |
| TIEPVLAEMFMG | 107 | DKETFELGLFDR | 108 |
| | | FSGVRGVYESRT | 109 |
| | | PDDAPMHSTRVE | 110 |

TABLE 3

| Peptide Sequence | SEQ ID NO |
| --- | --- |
| STGLMVDFLEPG | 91 |
| AKTFGLEHGCEA | 95 |
| GGTVEVWSIKGG | 115 |
| DHFSQAGSSNHH | 116 |
| DDPVTPVIDFGK | 117 |
| RDGLIDFVVAGT | 118 |

SEQ ID NO: 1 demonstrated dose-dependent binding with MAb in the ELISA of Example 2. This peptide was also inhibitory for MAb NS 19-9 binding to the synthetic multivalent SA-Le$^a$-polyacrylamide (PAA) matrix conjugate neoglycoprotein (Glycotech, Inc., Rockville, Md.) which contains the cognate oligosaccharide determinant. This implies that the sequence DLWDWVVGKPAG [SEQ ID NO: 1] represents a solvent-accessible epitope. The 50% inhibitory concentration (IC$_{50}$) value of SEQ ID NO: 1 was calculated to be 700 $\mu$M by competition ELISA [see, e.g., Blaszczyk et al, 1984, *Arch. Biochem. Biophys.* 233:161–168]. Control peptides containing the same amino acid composition but in a scrambled sequence failed to block antibody binding, indicating that the inhibitory effects of the native sequences are not due to nonspecific effects. Further, although SEQ ID NO: 1 exhibits relatively low-affinity binding with the antibody, a strong binding signal was observed on the Western blots when the peptide sequence was expressed in the context of thioredoxin. Without wishing to be bound by theory, this might be a reflection of structural constraints of the inserted peptide imposed by thioredoxin as compared with the conformation of the peptide in solution or in solid phase.

EXAMPLE 5

Molecular Basis for Peptide Binding to Anti-Lewis Antigen Antibodies

The molecular basis for peptide binding to anti-Lewis antigen antibodies was determined using the LIGAND- DESIGN (LUDI) program (Biosym Technologies, San Diego, Calif.) [Bohm 1992, *J. Comput. Aided Mol. Des.* 6:593–606]. This program searches a molecular library for fragments representative of the amino acids in the target peptide sequence. The program then positions the fragments within the combining site devoid of steric conflicts.

Previously, a molecular basis for interaction of LeY tetrasaccharide and MAb BR55-2 binding site was elucidated using molecular modeling [Blaszczyk-Thurin et al., 1996, *Protein Engineering* 9:101–113]. Modeling studies of the APWLYAGP [SEQ ID NO: 83] sequence mimicking LeY carbohydrate in the combining site of the anti-LeY antibody B3 [Murali and Kieber-Emmons, 1997, *J. Molec. Rec.*, 10:269–276] indicate that the putative contact residues APWLYA of SEQ ID NO: 83 adopt a turn conformation. Such a conformation is also projected for residues displayed in the constrained library.

In order to establish how the putative APWLY sequence of SEQ ID NO: 83 mimics LeY binding to B3, the pentapeptide sequence was "fitted" into the B3 combining site using the LUDI program. Using this program, the APWLY sequence of SEQ ID NO: 83 was modeled such that the Trp (W), Tyr (Y), Leu (L) and Ala (A) residues occupied relative positions as the identified LUDI fragments. Judicious positioning relied upon intermolecular interaction calculations in which several potential binding modes of the peptide were ranked according to the stability of the complex.

In the most stable conformation, the AP residues occupied a similar position to the LeY GlcNAc residue. This positioning indicates that the proline residue mimics the spatial position of the glucose unit of GlcNAc, while the Ala methyl group is positioned similarly to the terminal methyl group of GlcNAc's N-acetyl. The Trp residue occupies a volume associated with the Fucα 1,3 moiety, and the Leu residue occupies the volume of the β Gal moiety and has the hydrophobic interaction of β Gal. The Tyr residue occupies a position not associated with LeY binding to B3. The computer modeling disclosed that the low energy binding mode conformation adopts a turn region similar to that observed for the YPY motif in binding to ConA [Kaur et al., 1997, *J. Biol. Chem.* 272:5539–5543]. This conformation lends itself to the Tyr residue of the peptide to potentially interact with several residues in CDR2 of the heavy chain of B3 that include Asp H53, Ser H52, Ser H55, or Ser H56. These residues are different in BR55-2, which does not bind the monovalent APWLYGPA [SEQ ID NO: 121] peptide in a series of ELISA assays.

More importantly, energy optimization of the positioned peptide identified similar functional groups within the B3 combining site in contact with the peptide and carbohydrate tetrasaccharide core of LeY. Therefore, this analysis provides a strategy for determining the molecular basis for antigenic mimicry of particular motifs, providing a unique perspective of how a peptide sequence fits into the antibody or a receptor combining site, competing with a native antigen. This approach also enables the design of therapeutic compounds which more effectively compete with the native carbohydrate ligand for binding to cell adhesion molecules.

The above-disclosed approach was further extended to determine the types of motifs that bind to BR55-2 and whether such motifs could be isolated with BR55-2 from a peptide phage screen. Identification of such peptides as motifs would be a first step in to improving upon antigenic mimicry for LeY. Search of the LUDI database using the modeled structure of BR55-2 identified the motifs YPY, YRY and WRY, which are known to mimic various carbohydrate subunits, as interacting with BR55-2 and also identified a non planar-X-planar type motif, FSLLW [SEQ ID NO: 114], as possibly interacting. Thus, non-overlapping residue types were identified using the LUDI program as in the B3 studies. A computer-generated space filling model was generated which depicted the identification and placement of an optimized "FSLLW" amino acid motif in the combining site of anti-LeY monoclonal antibody BR55-2 in contrast to LeY positioned in the BR55-2 combining site. The topological similarity is very good. This peptide competes with LeY for BR55-2 binding. These data further demonstrate another method to develop peptide mimotopes that are specific. This method may be extended to identify motifs mimicking SA-LeX and SA-Le$^a$ using the crystal structure of the lectin domain of E-selectin in optimizing respective mimotopes.

EXAMPLE 6

Identification of Sequences Critical for MAb Binding and an SA-Le$^a$ Mimic with Higher Antibody Binding Affinity To analyze amino acid residues that are critical for NS19-9 recognition, an array library of 163 unique peptides was generated by systematic amino acid replacement in which each position of the starting peptide DLWDWV-VGKPAG [SEQ ID NO: 1] was replaced by other L-amino acids. In addition, peptides were synthesized with simultaneous incorporation of multiple amino acids or with truncation of specific regions.

The peptide array of 163 unique peptides was generated by substituting all amino acids for each individual amino acid in lead peptide (DLWDWVVGKPAG [SEQ ID NO: 1] identified by combinatorial library panning with MAb NS19-9. An array of synthetic 12-mer peptides was synthesized using 90×130 mm polyethylene glycol-modified cellulose membrane functionalized with approximately 4 nmole/mm$^2$ amino groups, manufactured by Abimed (Lagenfeld, Germany). Standard Fmoc chemistry was used according to the manufacturer's instructions [Frank, R., 1992, *Tetrahedron* 48, 9217–9332]. The protected and activated amino acids were spotted using an Abimed ASP 422 robotic arm. All washing, dyeing and deprotection steps were done manually. The activated C-terminal amino acids were spotted leaving 10 mm space in each direction, at the concentration of 0.5 M in N-methyl pyrrolidone. A volume of 0.5 ml provides spot of 7–8 mm in diameter. Activation of the amino acids with dicyclohexyl-carbodiimide and N-hydroxy-benzotriazole was done 30 minutes before spotting. After each coupling cycle, the paper was washed with 12% acetic anhydride dissolved in N,N'-dimethylformamide (DMF) twice for a total of 10 min to endcap all unreacted amino groups. Repetitive removal of the Fmoc groups was achieved by two treatments with 20% piperidine in DMF for 5 and 10 min, respectively. The second and consecutive amino acids were coupled in a 1.1 molar excess, and were spotted 3–4 times depending upon the outcome of the bromophenol blue assay of the couplings.

After the coupling and deprotection steps, the membrane was washed thoroughly with DMF and ethanol, dried and stained with bromophenol blue dissolved in DMF. After successful coupling the paper remains colorless; after successful deprotection steps the peptide dots turn deep blue. The coupling steps were repeated until all peptide spots remained colorless. The N-terminal amino acids at the end of the syntheses remained uncapped. Final removal of the side-chain protecting groups was performed by washing the paper with a mixture of 12.7 ml trifluoroacetic acid, 3.7 ml m-cresol, 3.7 ml thioanisole, 3.7 ml water and 3.7 ml ethanedithiol. After cleavage, the paper was washed several times with ethyl alcohol, DMF, water and methyl alcohol, and dried.

The peptide array library was tested for binding of MAb NS19-9. The cellulose filter was blocked with 5% non-fat milk in phosphate buffered saline (PBS). for 1 hour at room temperature followed by washing with PBS. Filters were incubated with goat anti-mouse immunoglobulin G conjugated with horse radish peroxidase (1 µg/ml) for 1 hour. Filters were washed five times in PBS-T (0.05% Tween in PBS, v/v) and developed using a chemiluminescence reagent followed by autoradiography as described in Western blot.

After probing of the membrane containing peptide spots with NS19-9 followed by chemiluminescence detection with a peroxidase-labeled anti mouse immunoglobulin G antibody, the peptide sequence was scanned by substitution of each amino acid with other L-amino acids by spot synthesis. Resulting peptides were tested for MAb NS19-9 binding or a varying number of amino acids were truncated. The number of peptides was 163 (6 raws, 27 spots each). Spot analysis revealed a distinct pattern of key residues important for binding and, therefore, sensitive to substitution while other residues tolerated replacement by a variety of amino acids.

Comparison of the signal intensities of the array scan revealed that the critical residues for binding were clearly identified within the N-terminal half of the DLWDWVVGKPAG peptide [SEQ ID NO: 1] as determined by the lack of antibody binding to substituted peptides (Table 4). In contrast, most of the substitutions within the C-terminus were tolerated (amino acids 6 to 12), not influencing MAb binding. These results indicate that the N-terminus is clearly involved in specific interaction with NS19-9. Most substitutions of residues 2 to 5 abolished NS19-9 binding, with Trp3 and Trp5 being the most critical. Identical sets of amino acids (His, Tyr, Ala, Asp, Glu, Lys, Arg, Ser) were shown to completely abolish antibody binding while Met significantly decreased the signal upon replacement of either of these residues (Trp 3 and 5). Similarly, substitutions of Leu2 with Ala, Asp, Tyr, Glu, Lys, Arg, and Ser as well as substitution of Asp4 with Glu, Ser, Pro, Val, Met, and Tyr completely abolished MAb binding. All peptides generated by truncation of amino acids 2 to 8 from the N-terminal of the peptide were no longer recognized by the antibody. Furthermore, when the 2–6 amino acid segments covering the key residues involved in antibody binding identified by the single amino acid substitutions were incorporated into the peptide, such a replacement always resulted in abolished binding. Most substitutions upstream from position 5 (positions 6–9) allowed for MAb binding with no evident preference for substituted amino acids. Although substitution analysis failed to identify significant differences in binding as a result of substitution of residues 9–12 within the C-terminal half of the peptide, MAb did not detect truncated peptides within this region implying the importance of the C-terminus for MAb binding. Table 4 lists the amino acid substitutions within peptide DLWDWVVGKPAG [SEQ ID NO: 1] that significantly decrease or abolish binding of Mab NS19-9 using the peptide array.

TABLE 4

| Peptide Sequence | SEQ ID NO |
|---|---|
| DLWDWVVGKPAG | 1 |
| DAWDWVVGKPAG | 2 |
| DDWDWVVGKPAG | 3 |
| DYWDWVVGKPAG | 4 |
| DEWDWVVGKPAG | 5 |
| DKWDWVVGKPAG | 6 |
| DRWDWVVGKPAG | 7 |
| DSWDWVVGKPAG | 8 |
| DLHDWVVGKPAG | 9 |
| DLYDWVVGKPAG | 10 |
| DLFDWVVGKPAG | 11 |
| DLMDWVVGKPAG | 12 |
| DLADWVVGKPAG | 13 |
| DLEDWVVGKPAG | 14 |
| DLDDWVVGKPAG | 15 |
| DLKDWVVGKPAG | 16 |
| DLRDWVVGKPAG | 17 |
| DLSDWVVGKPAG | 18 |
| DLWEWVVGKPAG | 19 |
| DLWSWVVGKPAG | 20 |
| DLWPWVVGKPAG | 21 |
| DLWVWVVGKPAG | 22 |
| DLWMWVVGKPAG | 23 |
| DLWMWVVGKPAG | 24 |
| DLWDHVVGKPAG | 25 |
| DLWDYVVGKPAG | 26 |
| DLWDMVVGKPAG | 27 |
| DLWDAVVGKPAG | 28 |
| DLWDDVVGKPAG | 29 |
| DLWDEVVGKPAG | 30 |
| DLWDKVVGKPAG | 31 |
| DLWDRVVGKPAG | 32 |
| DLWDSVVGKPAG | 33 |
| DLWDWLVGKPAG | 34 |
| DLWDWYVGKPAG | 35 |
| DLWDWAVGKPAG | 36 |
| DLWDWSVGKPAG | 37 |
| DLWDWVLGKPAG | 38 |
| DLWDWVAGKPAG | 39 |
| DLWDWVDGKPAG | 40 |
| DLWDWVDCKPAG | 41 |
| DLWDWVDPKPAG | 42 |
| DLWDWVDDYPAG | 43 |
| DLWDWVDDFPAG | 44 |
| DLHE | 45 |
| DLWEHL | 46 |
| LDWEWVVGKPAG | 47 |
| DLDL | 48 |
| EIHDWVVGKPAG | 49 |
| DLWEHL | 50 |
| LDDDWVVGKPAG | 51 |
| EIHEWVVGKPAG | 52 |
| DLWDHLLA | 53 |
| LDDLWVVGKPAG | 54 |
| EIHEHLVGKPAG | 55 |
| WDWVVGKPAG | 56 |
| DWVVGKPAG | 57 |
| WVVGKPAG | 58 |
| VVGKPAG | 59 |
| VGKPAG | 60 |
| GKPAG | 61 |
| KPAG | 62 |

Comparison of signal intensities on the peptide array revealed that some substitutions led to enhanced NS19-9 binding allowing for identification of several peptides with increased binding affinity to the antibody (Table 5). Improvement of peptide binding was achieved mainly by substitution of residues 5 to 12 within the lead peptide, whereas no amino acid exchange at N-terminus (residues 1–4) led to the increased binding. The replacement of residues with amino acids containing polar groups such as Glu and Asp showed clearly an enhancing effect at the C-terminus but not the N-terminus.

Array analysis failed to reveal significant differences in the binding intensities between the peptides substituted at different positions, suggesting that single substitution at any position in this region with carboxyl groups can enhance the interaction with the MAb binding site. In addition, substitutions with Ile, Ala and Ser also improved MAb binding. Similarly, the simultaneous replacement of several residues with clusters of amino acids upstream from position 6 demonstrated enhanced binding. The highest intensity signal was, however, observed with peptide DLWDEVVGKPAG [SEQ ID NO:63] containing a single substitution at position 5 with Phe.

Table 5 lists the amino acid substitutions within peptide DLWDWVVGKPAG [SEQ ID NO: 1] that increase the binding of MAb NS19-9 using the peptide array.

TABLE 5

| Peptide Sequence | SEQ ID NO |
| --- | --- |
| DLWDFVVGKPAG | 63 |
| DLWDWVIGKPAG | 64 |
| DLWDWVVAKPAG | 65 |
| DLWDWVVSKPAG | 66 |
| DLWDWVVEKPAG | 67 |
| DLWDWVVDKPAG | 68 |
| DLWDWVVGEPAG | 69 |
| DLWDWVVGDPAG | 70 |
| DLWDWVVGKEAG | 71 |
| DLWDWVVGKDAG | 72 |
| DLWDWVVGKPDG | 73 |
| DLWDWVVGKPAD | 74 |
| DLWDWVKEKPAG | 75 |
| DLWDWVLAKPAG | 76 |
| DLWDWVVGEDAG | 77 |
| DLWDWVVGKPEK | 78 |
| DLWDWVKEEPAG | 79 |
| DLWDWVVGKDEK | 80 |
| DLWDWVVGEDEK | 81 |
| DLWDWVKEEDEK | 82 |

A distinct pattern of substitutions that led to increased or abolished signal intensities with respect to the C- and N-terminus suggests that the region close to the N-terminus night contribute to the specificity of the interaction with NS19-9. Amino acids close to the C-terminus appear to add significantly to the affinity of ligand binding.

EXAMPLE 7

Inhibition of Binding of MAb to the Carbohydrate with Synthetic Peptides Mimicking SA-Le$^a$ Structure DLWVDWVVGKPAG [SEQ ID NO:1] and DLWDFVVGKPAG [SEQ ID NO:63] were chemically synthesized and tested for their ability to compete to immobilized synthetic SA-Le$^a$-PAA neoglycoprotein. To determine whether peptide SEQ ID NO: 1 and peptide SEQ ID NO: 63 are true mimics of SA-Le$^a$, dose-response experiments were carried out in order to determine the concentration of peptides required for blocking of 50% of MAb binding to the native carbohydrate antigen ($IC_{50}$), as determined by competition ELISA (Example 3). Both peptides SEQ ID NOS: 1 and 63 blocked the binding of MAb NS 19-9 to the constant amount of carbohydrate antigen in a dose-dependent manner. The $IC_{50}$ for peptide SEQ ID NO: 1 blocking of MAb-SA-Le$^a$ binding was 700 $\mu$M. Peptide SEQ ID NO: 63 exhibited a more pronounced dose-dependent inhibition of the MAb-SA-Le$^a$ binding as compared with peptide SEQ ID NO: 1 as demonstrated by the calculated $IC_{50}$ value of 70 $\mu$M for peptide SEQ ID NO: 63.

Without wishing to be bound by theory, these data suggest that the peptide sterically interferes with MAb binding to carbohydrate antigen. The sequences DLWDWVVGKPAG [SEQ ID NO: 1] and DLWDFVVGKPAG [SEQ ID NO:63] represent solvent-accessible epitopes and the peptides represent cognate determinants for the antibody. No measurable blocking of anti-Le$^a$ MAb NS 19-9 binding was found with non-related peptide, indicating that the inhibitory effects of the native sequences are due to specific effects.

EXAMPLE 8

Inhibition of Neutrophil Recruitment in an Acute Inflammation Model In Vivo by a Peptido-Mimetic of SA-Le$^a$ The accumulation of neutrophils is a characteristic feature of acute and chronic inflammatory disease, and early steps in the recruitment of these cells to the site of inflammation depends upon E-selectin-mediated interaction. Thus, inhibition of neutrophil recruitment in vivo is an important test of the ability of potential therapeutic agents to inhibit E-selectin-mediated events. SA-Le$^a$ interaction with E-selectin is not relevant for adhesion of neutrophils, since neutrophils do not express SA-Le$^a$ on their surfaces. However, tumor cells have been demonstrated to prefer SA-Le$^a$ over SA-LeX in mediating E-selectin-dependent adhesion interactions with endothelial cells. Because SA-Le$^a$ binds to E-selectin, the adhesion-blocking ability of an SA-Le$^a$ peptido-mimetic was measured in a neutrophil-recruitment in vivo model of acute inflammation. Thus, this assay demonstrates that the administration of a SA-Le$^a$ mimicking molecule inhibits neutrophil recruitment, i.e., diminishes the influx of neutrophils into chemically irritated peritoneum in vivo.

The bioactivity of the 12-mer peptide SEQ ID NO: 1 which mimics the SA-Le$^a$ carbohydrate structure was determined by administering Zymosan™ intraperitoneally (i.p.) into mice [see, e.g., Martens et al. 1995, *J. Biol. Chem.* 270:21129–21136; Rao et al. 1994, *J. Biol. Chem.* 269:19663–19666], followed three hours later by an intravenous (i.v.) injection of peptide SEQ ID NO: 1 (1 mg). Neutrophils were harvested and counted one hour later. As shown in FIG. 1A, peptide treatment significantly ($P<0.001$) reduced the number of neutrophils in peritoneal lavage fluids. Control experiments using the same dose of "scrambled" peptide sequence, which did not bind to NS19-9 MAb, exhibited no decrease in neutrophil influx relative to PBS-injected mice.

Figure 1B:
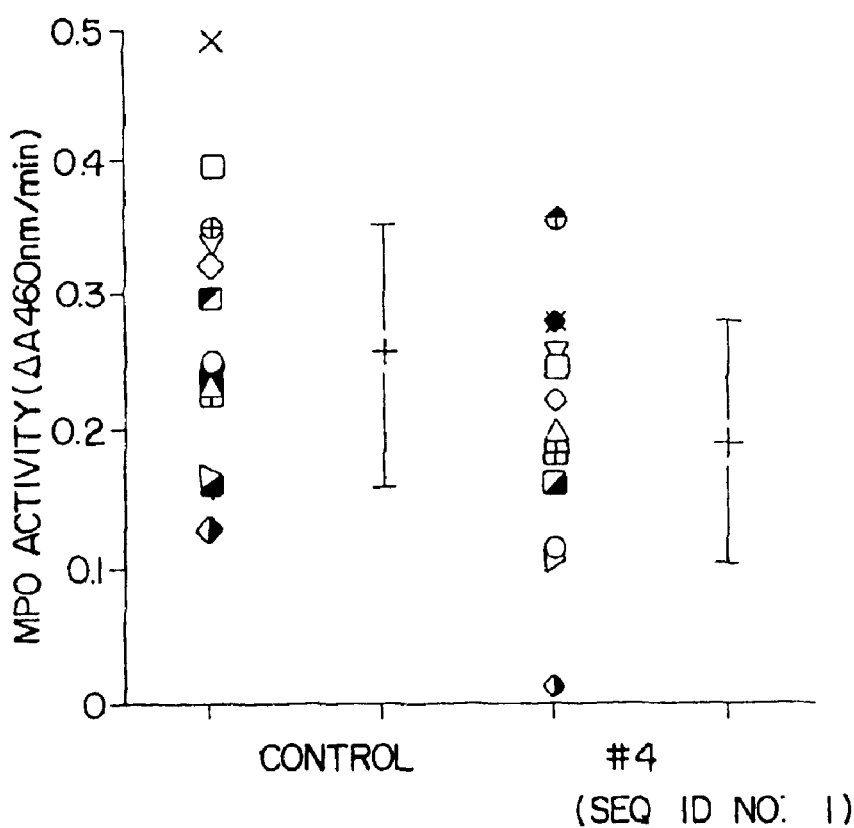
FIG. 1B is a diagram illustrating the myeloperoxidase activity in the collected neutrophils of the animals of FIG. 1A. Statistical analysis of the data using nonparametric unpaired t-test yielded p values <0.005 for this data.

To confirm these results, myeloperoxidase (MPO), activity, which is an enzymatic marker for neutrophils, was measured spectrophotometrically as an absorbance rate in the homogenates of collected cells [Bradley et al., 1982, *J. Invest. Derm.* 78:206–209]. Significant reduction of enzymatic activity ($P<0.005$) was observed in parallel with decreased neutrophil numbers assessed by total neutrophil count (FIG. 1B). The reduction in enzyme activity is apparently due to reduction in neutrophil recruitment in mice treated with peptide mimicking E-selectin ligand SA-Le$^a$. This peptide inhibits E-selectin function in vivo. Although peptide SEQ ID NO: 1 exhibited relatively low-affinity binding to MAb in vitro, $IC_{50}$ data from in vitro competition assays (Example 3) may not be relevant to the in vivo situation since the E-selectin blocking effect was clearly observed despite the low affinity demonstrated in vitro.

EXAMPLE 9

Peptido-Mimetics of E-Selectin Ligand

To identify peptides mimicking E-selectin ligand that may involve other than carbohydrate epitopes of the natural ligand, the 12-mer FLITRX fusion library was screened directly using E-selectin-IgG fusion protein, as described in Example 2. Among isolated peptides, the motif VLSP was found in 7 of 16 clones recovered. In addition, preferences for V/G and RR in the sites flanking the 5-amino acid motif were also found. In another group of peptides, a PGR sequence was found in 3 clones. As discussed above, peptides with different sequence motifs may mimic different topographical surfaces of the cognate carbohydrates or may bind to different binding areas of E-selectin combining site. Family I peptide sequences and Family II peptide sequences mimicking E-selectin ligand are reported in Table 6.

TABLE 6

| FAMILY I | | FAMILY II | |
|---|---|---|---|
| Peptide | SEQ ID # | Peptide | SEQ ID # |
| ASAVNLYIPTQE | 84 | DIRVEPGGGYTH | 94 |
| VYLAPGRISRDY | 95 | VYLAPGRISRDY | 95 |
| CTSHWGVLSQRR | 87 | APIHTYTGRARG | 96 |
| RVLSPESYLGPS | 91 | RHTCVRSCGHDR | 97 |
| VGNGVLMLGRRG | 90 | | |
| GNCRYIGLRQFG | 93 | | |
| RVLSPESYLGPA | 92 | | |

In summary, these data demonstrate that the conformation of small peptides can mimic the topography of the carbohydrate epitopes recognized by MAbs and by selectin. Carbohydrate mimotopes are effective in vivo in blocking selectin-dependent interactions, which can diminish leukocyte recruitment in inflammatory processes. The data demonstrate the feasibility of using small molecule antagonists isolated from combinatorial peptide libraries to block E-selectin function in vivo and to inhibit metastatic and inflammatory processes

EXAMPLE 10

Characterization of Carbohydrate Expression on Various Cell Lines

To develop tissue culture models of metastasis for in vitro and in vivo studies, phenotypes of various human and murine cell lines were characterized with respect to the expression of various carbohydrate structures implicated as ligands for selectins, e.g., SA-Le$^a$ and SA-LeX and also with respect to expression of LeY, which is a carbohydrate tumor-associated antigen not recognized by E-selectin. The expression of various carbohydrate antigens on human colon carcinoma, breast, gastric, and prostate carcinoma cell lines (originally obtained from ATCC, Rockville, Md.) was reported previously [Magnani et al., 1981, Science 212:55–56; Steplewski et al., 1985, Proc. Natl. Acad. Sci. USA 82:8653–8657; Blaszczyk-Thurin et al., 1987, J. Biol. Chem. 262:372–379; Blaszczyk et al., 1985, Proc. Natl. Acad. Sci. USA 82:3552–3556; Hansson et al., 1983, J. Biol. Chem. 258:4091–4097; Blaszczyk et al., 1985, Proc. Natl. Acad. Sci. USA 82:3552–3556; Blaszczyk-Thurin et al., 1988, Biochem. Biophys. Res. Commun. 151:100–108].

This expression was re-examined and confirmed using fluorescence-activated cell sorting (FACS) using specific MAbs developed at the Wistar Institute (Philadelphia, Pa.). Expression of surface carbohydrate ligands did not change as a function of proliferation in vitro, confirming the stability of the phenotype. Approximately 90–100% of cells obtained from human gastrointestinal adenocarcinoma lines SW948, SW1116, SW480, S180, HT29, Colo 201 and KATOIII and mammary adenocarcinoma cells MCF-7, SkBr5, SkBr3 and BT20 uniformly expressed both SA-Le$^a$ and SA-LeX structures at very high levels. Similarly, all cell lines demonstrated cell surface expression of LeY determinant, although expression levels varied among the cell lines.

Thus, these cell lines were the most suitable for the study of adhesion to EC in vitro and for an orthotopic tumor model in which immunodeficient mice may be inoculated with human tumor cells. The expression of SA-LeX in SW620 cells was below the level of detection, but the cells were uniformly and strongly stained for SA-Le$^a$. Thus, SW620 cells should be very useful in vivo evaluation of the contribution of SA-Le$^a$ to tumor cell colonizing ability in the absence of SA-LeX.

An autologous model of tumor metastasis is preferred for in vivo studies in which murine tumor cells derived from the same murine background may be inoculated to form metastases. Several murine tumor cell lines such as MethA sarcoma, G1261 glioblastoma, CT26 colon carcinoma, B16F1 and B16F10 melanoma clones obtained from DCTDC Tumor Repository (NCI Frederick, Md.) and murine breast adenocarcinoma 66.1, JC, 410.1 cell lines provided by Dr. Amy Fulton (university of Maryland, Baltimore, Md.) were characterized with respect to the expression of Lewis antigens. MethA clone #34 was isolated from the original MethA cell line cloned by limiting dilution and was determined to express SA-LeX antigen on 100% of cells as compared with only approximately 30% cells in the original cell line. All cell lines expressed SA-LeX except B16F1 and B16F10 variants, whereas no SA-Le$^a$ expression was observed among any cell lines. Therefore, MethA #34 is suitable to evaluate the role of SA-LeX mimicking peptides in inhibiting adhesion of tumor cells in vitro and in vivo.

A panel of tumor cells such as pancreatic PAN02, PAN03, colon CT38, CA51, mammary EMT-6, E0771, 755, lung ASBXIV, transitional bladder FCB and melanoma HP(Jax) (DCTDC Tumor Repository) was assembled. These cells were continuously analyzed with respect to the expression of SA-LeX, SA-Le$^a$, and LeY determinants. Moreover, expression vectors are available which contain α1,3/4 fucosyltransferase, (α1,3/4FTIII) cDNA [Seed, 1987, Proc. Natl. Acid. Sci. USA 84:8573–8577], and α1,2 fucosyltransferase cDNA (α1,2FT) [Sun et al., 1995, Proc. Natl. Acad. Sci. USA 92:5724–5728]. Tumor cell lines were generated which express SA-Le$^a$ and LeY transfection, respectively, using transfection procedures. Further, 1–2×10$^5$ Meth A and B16 tumor cells were sufficient to form countable lung metastasis within 2 to 3 weeks following intravenous (i.v) tumor cell inoculation in Balb/c and C57B1/6 strains of mice, respectively.

EXAMPLE 11

E-Selectin-Independent Adhesion of Adenocarcinoma Cells

Figure 2A:
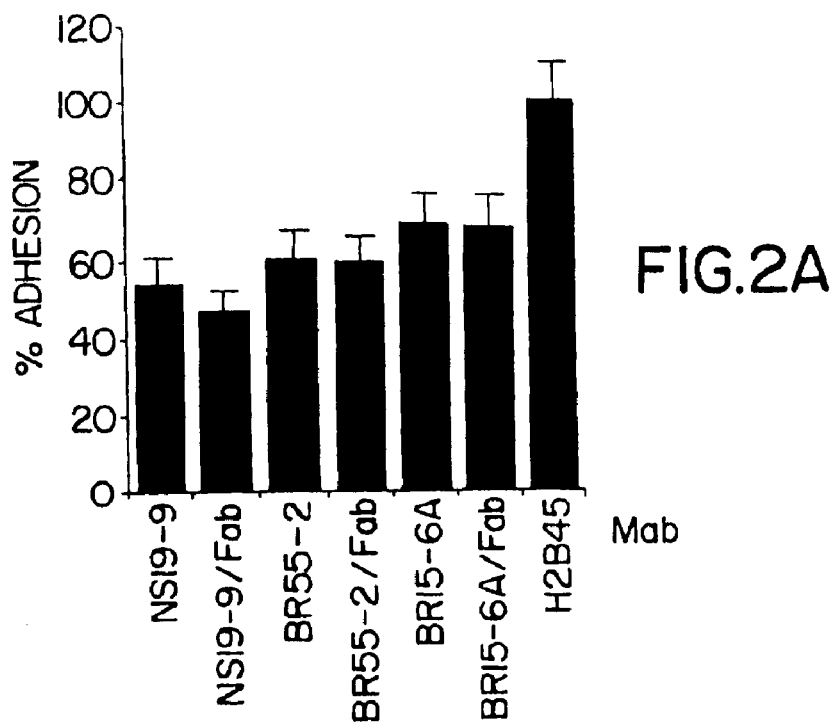
FIG. 2A is a bar graph demonstrating the E-selectin-independent adhesion of human mammary adenocarcinoma cells SkBr5 to the human endothelioma cell line ECV-304. SkBr5 and HUVEC cells were allowed to adhere for 15 minutes in the continuous presence of MAbs and MAb F(ab)$_2$ fragments (marked in the graph) at 40 pg/ml. Control anti-influenza hemagglutinin MAb H24135 was used at the same concentration. The results represent the percentage (%) of adherent cells in the presence of specific MAb as compared to control anti-influenza hemagglutinin MAb H24135. Results are reported as means±standard error (SE) of five independent experiments.
Figure 2B:
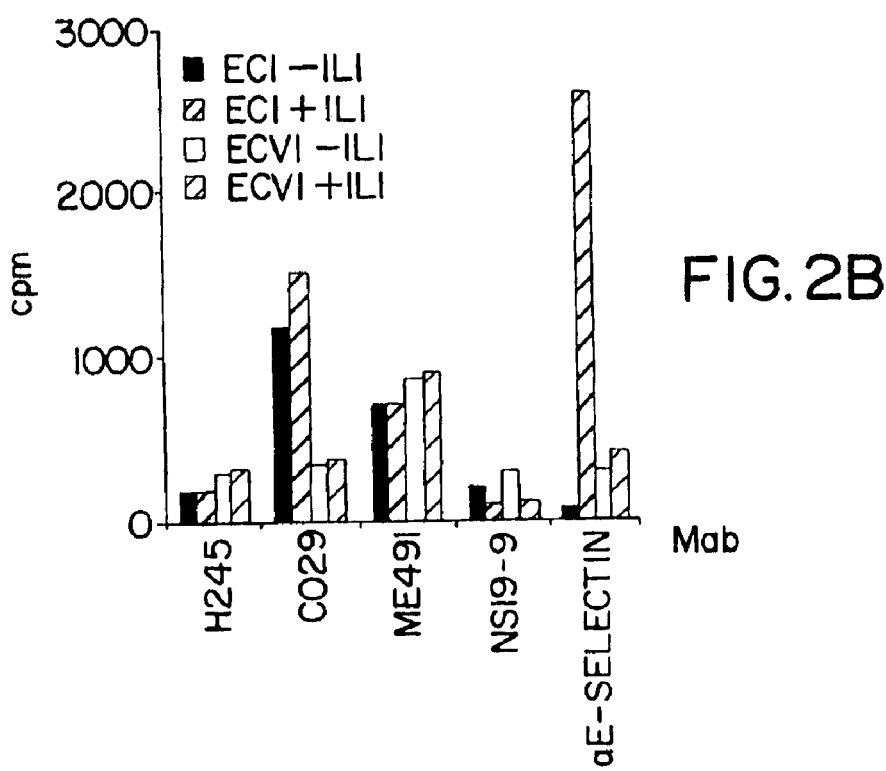
FIG. 2B is a graph depicting the representative data of the expression of various antigens on the surface of cells in the absence (−) or presence (+) of the inflammatory cytokine, Interleukin-1, as determined by MAbs binding in radioimmunoassay (RIA) with monolayer ECV-304 cells. The presence of the following antigens was detected using the MAbs indicated: SA-Le$^a$(MAbNS19-9), CD63 (MAb C029 and ME491), E-selectin (specific MAb anti-ELAM-1, British Bio-Technology, UK), and anti-influenza virus hemagglutinin negative control (MAb H24135).

Tumor cell adhesion to EC monolayers was investigated in vitro as described in Iwai et al., cited above, as a model for metastatic invasion. The data disclosed herein demonstrate that various mammary adenocarcinoma cells attach to TNF-α or IL-1β cytokine-activated human umbilical cord vein endothelial cells (HUVEC) via an E-selectin-independent mode. Further, the data demonstrate that human breast adenocarcinoma cell lines, SkBr5 and SkBr3, but not colon adenocarcinoma cells LS 180, SW1116 and SW948, adhere to TNF-α-stimulated EC and that this process is mediated by E-selectin as determined by the inhibitory effect of anti-E-selectin MAb as well as NS 19-9 MAb specific for SA-Le$^a$ (FIG. 2A). Antibodies BR55-2 and BR15-6A directed to LeY significantly decreased the adhesion in a dose-dependent fashion, implicating the involvement of LeY in adhesion of these breast carcinoma cells (FIG. 2A). These cells also adhered to the spontaneously transformed human endothelioma cell line ECV-304 in an LeY-dependent way. ECV-304 cells unlike primary HUVEC, did not express E-selectin even in the presence of inflammatory cytokines as assayed by radioimmunoassay [Blaszczyk et al. 1984, Cancer Res. 44:245–253] using anti-E-selectin antibody (FIG. 2B). These data indicate that different human adenocarcinoma cells interacted with EC via E-selectin-mediated and E-selectin-independent pathways.

The data disclosed are in agreement with previously published reports that some invasive breast carcinoma cells do not interact with TNF-α-stimulated EC under dynamic conditions, but adhere to resting and stimulated EC via an E-selectin-independent mode following static incubation [Iwai et al, cited above; Tozeren et al., cited above; Miyake et al., cited above; Garrigues et al., cited above; Dottke and Loibner, cited above]. ECV-304 endothelioma cells which have lost the ability to express E-selectin, are a useful model for in vitro studies of E-selectin-independent adhesion of tumor cells to EC and the role of this pathway in the establishment of metastasis.

EXAMPLE 12

Figure 3:
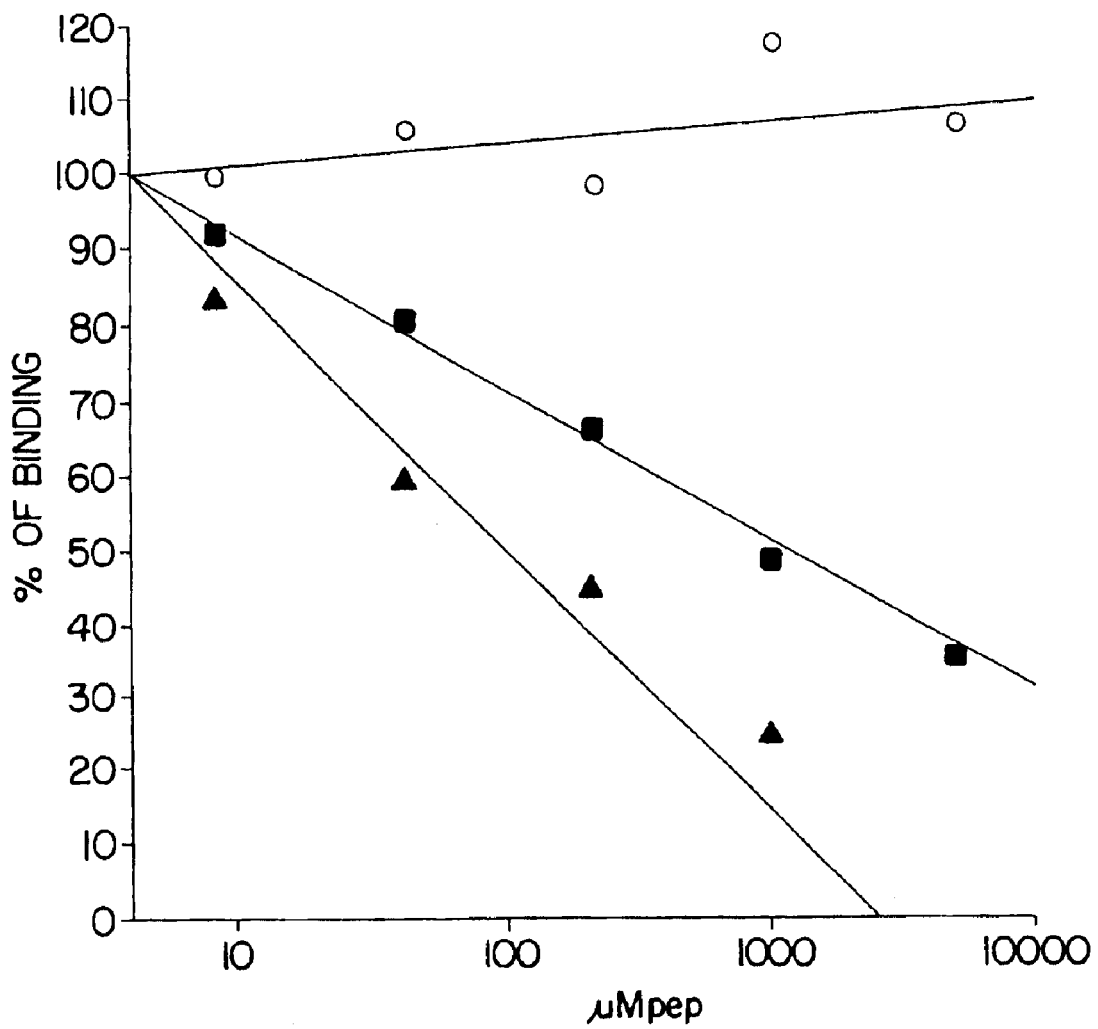
FIG. 3 is a graph illustrating the effect of Trp5 substitution with Phe in peptide DLWDWVVGKPAG [SEQ ID NO: 1] resulting in peptide DLWDFVVGKPAG [SEQ ID NO: 63] on binding of SA-Le$^a$ specific MAb NS19-9. Constant amounts of Mab were incubated with increasing amounts of peptides and binding of free antibody to carbohydrate SA-Le$^a$ was measured by enzyme linked immunosorbent assay. Results show competitive inhibition of MAb binding to solid phase SA-Le$^a$ polyacrylamide matrix (SA-Le$^a$-PAA) by 12-mer peptides DLWDWVVGKPAG (■) [SEQ ID NO: 1] and DLWD<u>F</u>VVGKPAG (▲) [SEQ ID NO: 63] with respect to the MAb binding without peptide (100% of binding) and a negative control unrelated peptide (○).

Competition of DLWDFVVGKPAG Peptide [SEQ ID NO:63] with SA-Le$^a$ for MAb Binding The lead peptide DLWDWVVGKPAG [SEQ ID NO:1] and the array selected peptide DLWDFVVGKPAG [SEQ ID NO: 63] were synthesized individually and their binding specificities to NS19-9 MAb were assayed by competitive solid phase enzyme linked immunosorbent assay (Example 3), with the results as shown in FIG. 3.

Both peptides inhibited binding of MAb NS19-9 to a solid phase adsorbed cognate carbohydrate antigen SA-Le$^a$ in a dose dependent manner. IC$_{50}$ of the substituted peptide DLWDFVVGKPAG [SEQ ID NO: 63] was established at 70 μM whereas the IC$_{50}$ of the lead peptide DLWDWVVGKPAG [SEQ ID NO:1] was 700 μM (FIG. 3). This 10-fold lower IC$_{50}$ value for the array-selected peptide reflects a higher binding affinity of this peptide as compared to the lead peptide. These data suggest the DLWDFVVGKPAG peptide [SEQ ID NO: 63] displays a better fit into MAb binding site as compared with the original peptide. No significant binding of MAb NS19-9 was observed with unrelated peptide in the concentration range up to 5 mM (FIG. 3).

EXAMPLE 13

Secondary Structure of Peptides Mimicking Carbohydrate

Figure 4:
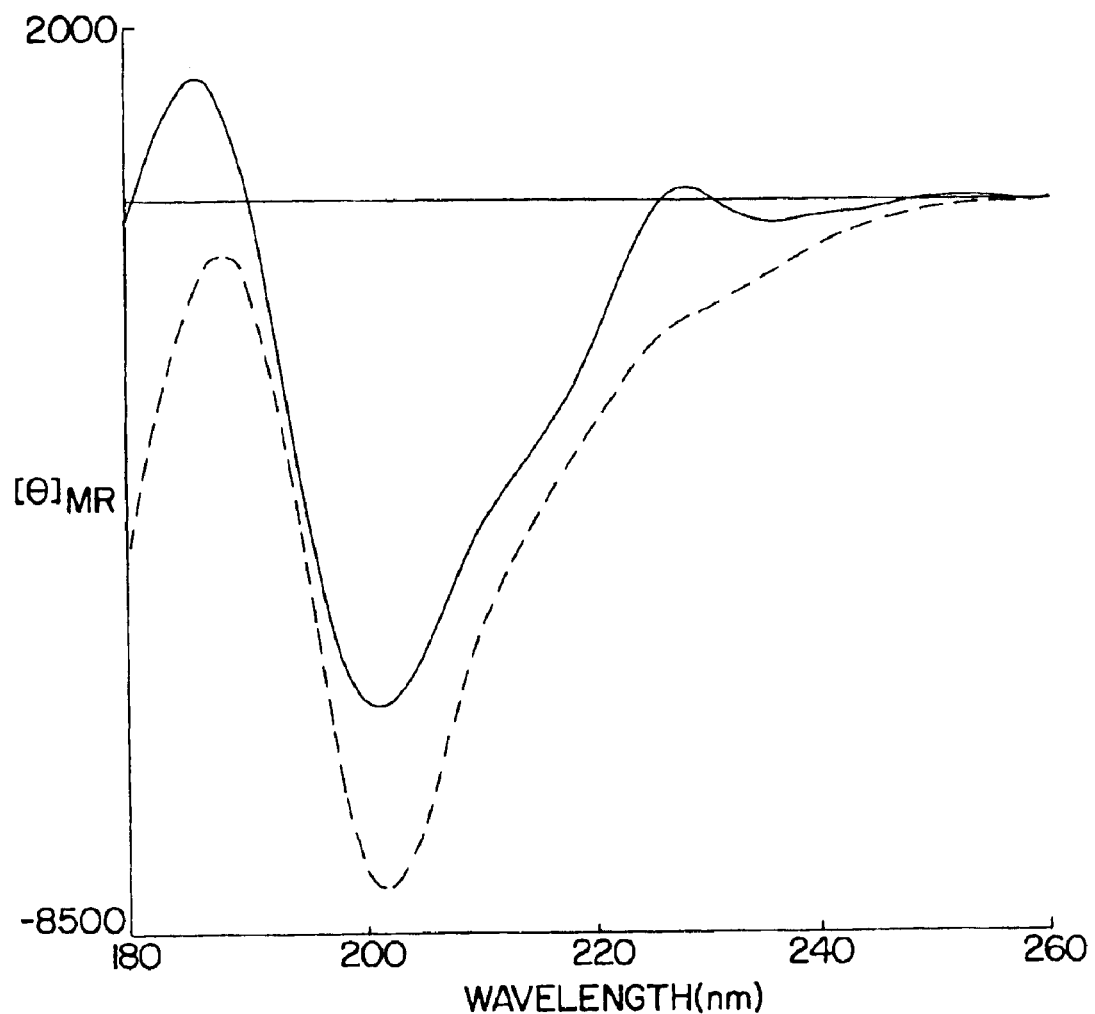
FIG. 4 is a circular dichroism (CD) spectra comparing dodecapeptides DLWDWVGKPAG (solid line) [SEQ ID NO: 1] and DLWD<u>F</u>VVGKPAG (---) [SEQ ID NO:63]. The spectra were recorded at 0.51 mg/ml for both peptides.

Secondary structure prediction, based on a neutral net algorithm [Chandonia, J. M., and Karplus, M., 1996, Protein Sci. 5: 768–774] indicated some propensity of both peptides DLWDWVVGKPAG [SEQ ID NO: 1] and DLWDFVVGKPAG [SEQ ID NO: 63] to assume extended or helical structures centered at the mid-chain WVVG and FVVG domains of SEQ ID NOS: 1 and 63, respectively (FIG. 4). The presence of β-pleated sheets was further supported by calculations based on the Fasman-Chou probability values [Fasman, G. D., 1985, J. Biosci. 8: 15–23], although these predictions placed the extended structure closer to the amino termini, with the C-terminal fragments showing reverse-turn conformations.

Low-resolution conformational analysis by CD supported these calculations. CD spectra were taken on a Jasco J720 instrument at room temperature in a 0.2 mm pathlength cell. Double distilled water and spectroscopy grade trifluoroethanol were used as solvents. The peptide concentration was 0.51 mg/ml, determined by quantitative reversed-phase HPLC. The algorithms provided by JASCO accomplished curve smoothing. Mean residue ellipticity is expressed in degrees cm$^2$/dmole by using a mean residue weight of 110. Because the secondary structures of the peptides by the current computer-assisted curve analyzing algorithms show a high error rate, the CD spectra evaluations were based on comparison with known peptide conformations [Woody, R. W. (1985) The Peptides, eds. Hruby, V. J. (Academic Press, Orlando), pp. 15–114].

In water both peptides exhibited negative bands at 201–202 nm indicative of mostly unordered structures, common for medium-sized peptides. However, the slight redshift from the generally observed 197–198 nm band for entirely random coils highlighted the presence of type I (III) β-turns. Comparison of the CD of the two peptides assigned an increased contribution of reverse-turns to the conformational equilibrium for peptide SEQ ID NO: 63, based on the minor redshift of both the 197 nm and the 202 nm bands. A negative shoulder, characteristic for turns, replaced the small positive band between 220 and 230 nm (indicative for random peptide structure). In contrast, peptide SEQ ID NO: 63 lacks a negative shoulder between 210 and 220 nm, clearly present for peptide SEQ ID NO: 1. Peptides and proteins in β-pleated sheets or type II β-turns exhibit negative bands in this wavelength region. Considering the secondary structural prediction, the presence of extended structure may be more likely than that of type II β-turns.

In the structure-inducing solvent 50% trifluoroethanol both ππ* bands for both peptides were reshifted, indicating the acquisition of more ordered structures, as expected (data not shown). The 227 nm positive band of the random coils for peptide SEQ ID NO: 1 disappeared, but the 216 nm negative β-pleated sheet band remained intact as did the 228 nm negative shoulder for peptide SEQ ID NO: 63, suggesting the random conformations were merely replaced by the signature structures (i.e., extended for peptide SEQ ID NO: 1 and turn for peptide SEQ ID NO: 63).

Nevertheless, the conformational differences may not represent casual correlations to antibody recognition. Both peptides DLWDWVVGKPAG [SEQ ID NO: 1] and DLWDFVVGKPAG [SEQ ID NO: 63] highlight the functional role played by the aromatic-X-aromatic motif within the peptide. It is possible that these structure types are realized within the antibody-combining site. This is consistent with modeling and crystal analysis of this motif type which suggested that these regions may adopt type I or type II turns within the antibody-combining site. Turn conformations appear to play an important role in E-selectin recognition based on structure activity relations of modified Ser-Glu dipeptides that bind to E-selectin. The increased binding of peptide SEQ ID NO: 63 with substitution of Phe for Trp suggests that the Phe directly contributes to MAb and that hydrophobic stacking interactions are important for increased antibody binding and consequently antigenic mimicry. This assertion is supported by X ray crystallographic and molecular modeling studies of carbohydrate mimicking peptides.

EXAMPLE 14

Inhibition of Tumor Metastasis

SA-Le$^a$ appears to mediate the adhesion of many carcinoma tumors to human umbilical vascular endothelial cells in multiple in vitro studies. An in vivo experimental metastatic model which permits investigation of SA-Le$^a$ supported adhesion of tumor cells to lung endothelium is performed as follows:

B16F10 murine melanoma cells do not naturally express E-selectin ligands SA-LeX or SA-Le$^a$ as demonstrated by FACS analysis, and are syngeneic with C57B1/6 haplotype (American Type Tissue Collection, Rockville, Md.). To manipulate these cells to express the SA-Le$^a$ structure on the tumor cell surface, the B16F10 cells were stably transfected with pCDNA-FTIII using Effectene (Qiagen, Chatsworth, Calif.) as recommended by the manufacturer. Plasmid pCDNA-FTIII is prepared by cloning HindIII and NotI-digested α1-3/4-fucosyltransferase cDNA (FTIII) obtained from the πH3M vector containing FTIII cDNA (Brian Seed, Massachusetts General Hospital, Boston, Mass.) was cloned into pCDNA3(neo) vector. FTIII fucosyltransferase is specific for both type 1 and 2 lactoseries oligosaccharide acceptor substrates and thus is capable of synthesizing both SA-Le$^a$ and SA-LeX, respectively. The resulting cell line, B16F10FTIII, expresses SA-Le$^a$ carbohydrate structure as demonstrated by flow cytometry analysis using MAb NS19-9 as compared to the parental B16F10, which did not show staining with this antibody.

The transfected cells were grown in the presence of G418 (500 μg/ml) (Gibco-BRL, Grand Island, N.Y.) for 10 days. To ensure the homogeneity of the transfected cells with respect to the expression of SA-Le$^a$, the cells were subjected to cell sorting using SA-Le$^a$ specific MAb NS19-9 followed by FITC-conjugated goat anti-mouse immunoglobulin. The resulting cell line B16F10FTIII appeared to express SA-Le$^a$ but not SA-LeX as assessed by FACS (not shown), suggesting that type 1 but not type 2 acceptors were available within the cells. Thus, the generated cell line made a suitable model to determine the role of SA-Le$^a$ in the metastatic process since the tumor cells are devoid of SA-LeX. The tumorigenic dose for the C57B1/6 syngeneic tumor cells was established by i.v. injection of various numbers of cells. A $1 \times 10^5$ dose was chosen for further experiments as countable lung metastases were observed after i.v. injection of $1 \times 10^5$ of B16F10FTIII cells expressing SA-Le$^a$ after 21 days.

The role of tumor cell adhesion to vascular EC via E-selectin and its ligand SA-Le$^a$ interaction in metastasis formation was established in vivo in two ways. First, to directly assess the role of E-selectin in tumor colonization in vivo, the ability of B16F10 murine melanoma cells expressing SA-Le$^a$ to colonize in the lung of E-selectin KO mice of C57B1/6 background [Staite, N. D. et al, 1998, *Blood*, 88: 2973–2979, and kindly provided by Dr. Daniel Bullard (University of Alabama at Birmingham, Ala.)] was determined in parallel with wild-type six- to 8-week-old C57B1/6 female mice (Jackson Laboratory, Bar Harbor, Me.). KO mice lack E-selectin expression.

Figure 5:
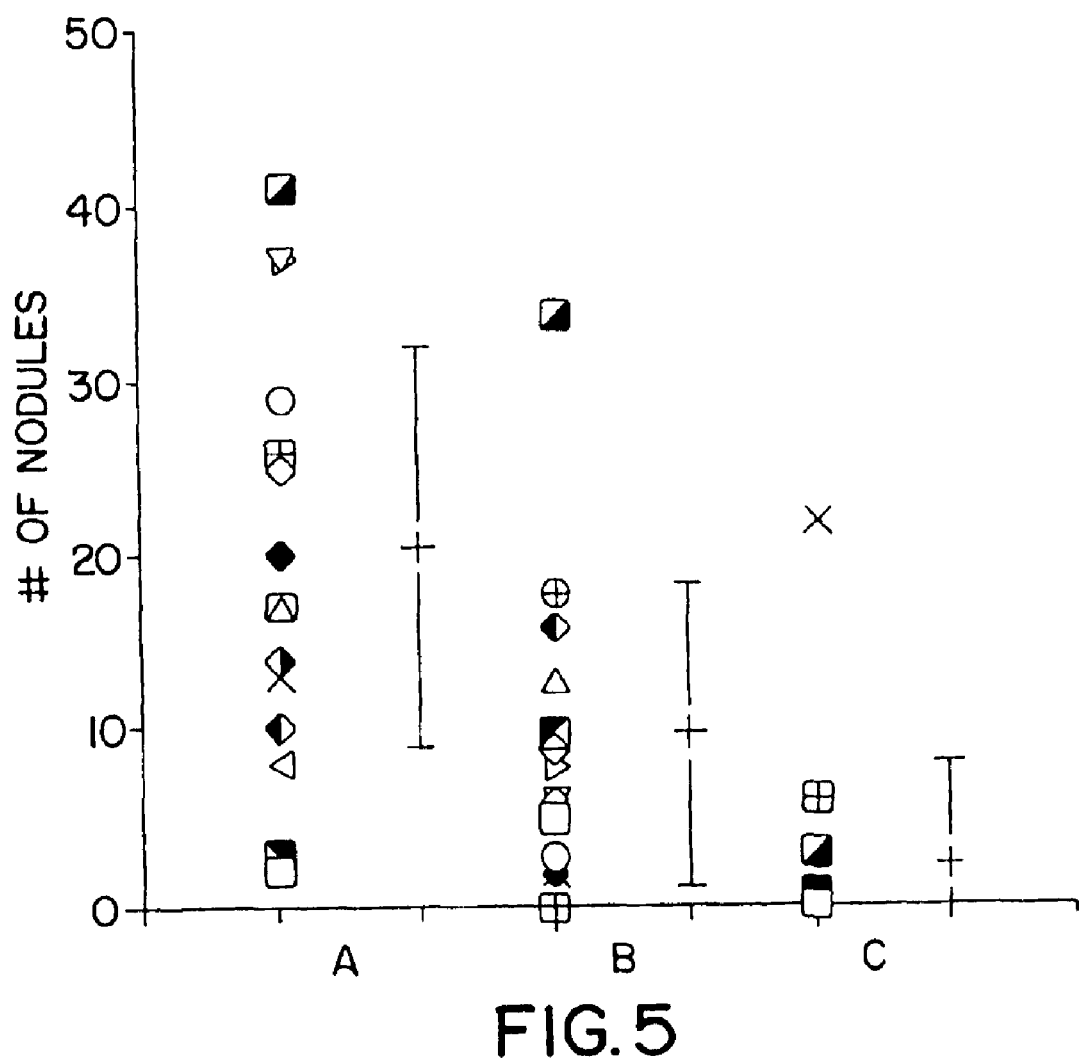
FIG. 5 is a graph illustrating the inhibition of lung experimental metastases with peptide DLWD<u>F</u>VVGKPAG [SEQ ID NO: 63]. Tumor cells were admixed with the specific or unrelated peptide solution (1 mg per mouse) and animals were inoculated with 1×10$^5$ B16F10FtlII tumor cells in 200 μl volume of PBS via tail vein. Results are from 4 experiments (5 mice in each group) are shown. Each dot represents enumerated tumor nodules in one lung in experimental group of C57B1/6 mice treated with the peptide (panel B), control group of C57B1/6 mice treated with unrelated peptide (panel A) and E-selectin knock-out (KO) mice of C57B1/6 background (panel C). Statistical analysis using a nonparametric unpaired t test gave a two-tailed p values <0.008 and 0.009 for animals treated with peptide and E-selectin KO, respectively, as compared to control group. The horizontal bars represent median values and vertical bars denote standard deviation.

B16F10FTIII cells positive for SA-Le$^a$ were grown in vitro in Iscove's culture medium supplemented with 10% FBS for 1 week before injecting into mice. Cells were collected and washed twice in Iscove's medium without serum and suspended in PBS. One$\times 10^5$ tumor cells in a volume of 200 μl in PBS were inoculated by intravenous (i.v.) route via tail vein. To test the effect of the peptide, animals were inoculated with a single dose of peptide at the time of tumor challenge. One mg of peptide was admixed with the tumor cells and together injected via i.v. route. Control animals received injection of tumor cells admixed with the same amount of unrelated peptide. Mice were euthanized after 3 weeks following tumor cells injection and lung and other organs were examined under dissecting microscope for the presence of tumor nodules. The lungs were excised and the number of nodules was enumerated for each animal without fixation of the lungs. Data were evaluated for statistical significance using a nonparametric unpaired two-tailed t test. The results are shown in FIG. 5.

Mice of both strains received i.v. injection of $1 \times 10^5$ B16F10FtIII tumor cells and mice were examined 3 weeks later. Only 20% of E-selectin deficient animals injected with tumor cells developed small numbers of lung metastasis while the rest of the E-selectin KO mice showed no detectable lung tumor nodules. Statistical analysis gave a P values <0.009 for E-selectin KO as compared to the control group (FIG. 4, A and C), respectively. Small nodules were observed in a few E-selectin KO mice that developed tumors whereas all animals in the control group developed multiple metastasis and some of them died earlier than 3 weeks. The results demonstrate that lung metastasis of tumor expressing SA-Le$^a$ antigen is completely abrogated in most of the genetically manipulated mice that lack expression of E-selectin, highlighting the critical role of E-selectin in mediating carcinoma metastasis in vivo.

To further test the hypothesis that SA-Le$^a$ expression supports adhesion of tumor cells to E-selectin on EC, the inhibitory effect of peptide mimicking SA-Le$^a$ antigenic structure DLWDFVVGKPAG [SEQ ID NO: 63] on lung colonization of B16F10FTIII cells was tested. One$\times 10^5$ tumor cells expressing SA-Le$^a$ were admixed with a solution containing 1 mg of the peptide DLWDFVVGKPAG [SEQ ID NO: 63], followed by administration of the mixture to groups of mice. Because peptides in general show rather short half-life in mouse serum, in the peptide inhibition studies in vivo the peptide was admixed with the tumor cells to sustain the highest transient concentration of peptide at the time of tumor cell arrival into the lung capillary system. Animals were euthanized after 21 days following tumor challenge and the number of metastasis was enumerated in each lung whereas, no metastatic growth was detected in the liver.

Administration of the peptide DLWDFVVGKPAG [SEQ ID NO: 63] abrogated on average 50% lung colonization of the B16F10FTIII induced tumor nodules developed in control animals; some mice being completely devoid of tumor nodules (FIG. 4B). The injection of the peptide 1 hour prior to tumor cells did not influence the rate of metastases formation in comparison with the peptide administered together with tumor cells. Animals treated with peptide showed metastases ranging from 0 to 20 per lung (median 9.9), whereas, animals in the control group developed multiple tumor nodules with the number of metastases per mouse ranging from 3 to 40 per lung (median 20.7) (FIG. 4B and 4A), respectively. The difference was highly statistically significant ($p<0.008$). In addition, B16F10FtIII cells in C57B1/6 mice developed large tumor masses with diffused infiltration of tumor cells and some mice died before the termination of the experiment (median 16 days). Mice that developed metastases, despite treatment with SA-Le$^a$ mimicking peptide, showed the presence of small tumor nodules and all survived the 3 week observation time.

These results suggest that the synthetic structural conformer mimicking SA-Le$^a$ antigen is able to significantly block the adhesion of tumor cells to vascular endothelium at the early stages of the multistep process, thus reducing tumor metastases. This finding strongly suggests that the interaction of SA-Le$^a$ carbohydrate tumor-associated antigen with E-selectin expressed on vascular EC is an important step in establishing tumor metastasis.

The disclosures of each and every patent, patent application, and publication cited herein are hereby incorporated herein by reference in their entirety. While the invention has been disclosed with reference to specific embodiments, it is apparent that other embodiments and variations of this invention may be devised by others skilled in the art without departing from the true spirit and scope of the invention. The appended claims to be construed to include all such embodiments and equivalent variations.

What is claimed is:

1. A peptide or polypeptide selected from the group consisting of: ASAVNLYIPTQE SEQ ID NO:84, VYLAPGRISRDY SEQ ID NO:85, VYLAPGRFSRDY SEQ ID NO:86, CTSHWGVLSQRR SEQ ID NO:87, RVLSPESYLGPS SEQ ID NO:88, VGNGVLMGRRG SEQ ID NO:90, RVLSPESYLGPA SEQ ID NO:92, GNCRYIGLRQPG SEQ ID NO:93, DIRVEPGGGYTH SEQ ID NQ:94, APIHTYTGRARG SEQ ID NO:96, and RHTCVRSCGHDR SEQ ID NO:97 which binds to a selectin and blocks binding between said selectin and a Lewis SA-Le$^a$ or SA-LeX antigen.

2. The peptide or polypeptide according to claim 1, which comprises a modification selected from the group consisting of (i) use of one or more D amino acids, (ii) insertion of a moiety which can provide a net positive charge at the N-terminus of said peptide or polypeptide, (iii) insertion of a spacer of greater than 3 amino acids interposed between the N- and C-termini to cyclize the peptide, (iv) insertion of a free hydroxyl on the C-terminus, (v) insertion of an amide or imide on the C-terminus, and (vi) insertion of a sequence of one or up to about 15 additional amino acids on the C-terminus.

3. A peptide or polypeptide selected from the group consisting of VGIWSVVSEGSR SEQ ID NO:102, RCSVGVPFTMES SEQ ID NO: 103, QDGVWEHVLEGG, SEQ ID NO: 104, DLWDWVVGKPAG SEQ ID NO: 1, VELSGRGGLCTW SEQ ID NO:105, VIGAASHDEDVD SEQ ID NO:106, TIEPVLAEMFMG SEQ ID NO:107, DKETFELGLFDR SEQ ID NO:108, FSGVRGVYESRT SEQ ID NO:109, PDDAPMHSTRVE SEQ ID NO:110, STGLMVDFLEPG SEQ ID NO:91, AKTFGLEHGCEA SEQ ID NO:95, GGTVEVWSIKGG SEQ ID NO:115, DHFSQAGSSNHH SEQ ID NO:116, DDPVTPVIDFGK SEQ ID NO:117, and RDGLIDFVVAGT SEQ ID NO:118 which binds to a selectin and blocks binding between said selectin and a Lewis SA-Le$^a$ or SA-LeX antigen.

4. The peptide or polypeptide according to claim 3, which comprises a modification selected from the group consisting of (i) use of one or more D amino acids, (ii) insertion of a moiety which can provide a net positive charge at the N-terminus of said peptide or polypeptide, (iii) insertion of a spacer of greater than 3 amino acids interposed between the N- and C-terminus to cyclize the peptide, (iv) insertion of a free hydroxyl on the C-terminus, (v) insertion of an amide or imide on the C-terminus, and (vi) insertion of a sequence of one or up to about 15 additional amino acids on the C-terminus.

* * * * *

UNITED STATES PATENT AND TRADEMARK OFFICE
CERTIFICATE OF CORRECTION

PATENT NO. : 6,960,566 B1
APPLICATION NO. : 09/831047
DATED : November 1, 2005
INVENTOR(S) : Blaszcyk-Thurin et al.

It is certified that error appears in the above-identified patent and that said Letters Patent is hereby corrected as shown below:

Title page,
Item [75], Inventors, add -- Thomas Kieber-Emmons, Newtown Square, PA --;
Item [73], Assignees, replace "Wister" with -- Wistar --.

Column 3,
Line 1, replace "firther" with -- further --;

Column 6,
Line 17, replace "DLWDWWGKPAG" with -- DLWDWVVGKPAG --;

Column 7,
Line 31, replace "VGIWSWSEGSR" with -- VGIWSVVSEGSR --;
Line 36, replace "LAEMMG" with -- LAEMFMG --;

Column 17,
Line 67, replace "3:883" with -- 33:883 --;

Column 18,
Line 12, replace "25:1078-1082" with -- 257:1078-1082 --;
Line 25, replace "arc" with -- are --;

Column 24,
Line 48, replace "carbodiimidc" with -- carbodiimide --;

Column 27,
Line 10, replace "DLWDEVVGKPAG" with -- DLWDFVVGKPAG --;
Line 41, replace "night" with -- might --;
Line 50, replace "DLWVDWVVDKPAG" with -- DLWDWVVGKPAG --;

Column 34,
Line 66, replace "claims to be" with -- claims are intended to be --;

UNITED STATES PATENT AND TRADEMARK OFFICE
CERTIFICATE OF CORRECTION

PATENT NO. : 6,960,566 B1 Page 2 of 2
APPLICATION NO. : 09/831047
DATED : November 1, 2005
INVENTOR(S) : Blaszcky-Thurin et al.

It is certified that error appears in the above-identified patent and that said Letters Patent is hereby corrected as shown below:

Column 69,
Lines 20 and 21, replace "GNCRYIGLRQPG" with -- GNCRYIGLRQFG --.

Signed and Sealed this

Eleventh Day of July, 2006

JON W. DUDAS
*Director of the United States Patent and Trademark Office*